United States Patent
Lee et al.

(10) Patent No.: US 7,795,299 B2
(45) Date of Patent: *Sep. 14, 2010

(54) NEO-TANSHINLACTONE AND ANALOGS AS POTENT AND SELECTIVE ANTI-BREAST CANCER AGENTS

(75) Inventors: Kuo-Hsiung Lee, Chapel Hill, NC (US); Xihong Wang, Chapel Hill, NC (US); Kenneth F. Bastow, Chapel Hill, NC (US); Tian-Shung Wu, Tainan (TW)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/355,309

(22) Filed: Jan. 16, 2009

(65) Prior Publication Data

US 2009/0118356 A1   May 7, 2009

Related U.S. Application Data

(63) Continuation of application No. 11/075,476, filed on Mar. 9, 2005, now Pat. No. 7,495,026.

(60) Provisional application No. 60/552,050, filed on Mar. 10, 2004.

(51) Int. Cl.
   *A61K 31/366* (2006.01)
   *C07D 493/04* (2006.01)
(52) U.S. Cl. ............ 514/453; 549/279; 549/42; 549/24; 548/421; 546/62; 514/285; 514/410; 514/432; 514/443
(58) Field of Classification Search ........ 514/453, 514/285, 410, 432, 443; 549/279, 24, 42; 546/62; 548/421
See application file for complete search history.

(56) References Cited

U.S. PATENT DOCUMENTS 7,495,026 B2 * 2/2009 Lee et al. ............ 514/453

OTHER PUBLICATIONS

Compound with RN 133591-99-8.*
PCT International Search Report for International Application No. PCT/US05/07634; Mailed Jul. 27, 2005.
Rajitha, B. et al.: Synthesis of Coumestrol Analogs as possible Antifertility agents. Indian J. Chem. Aug. 1986, vol. 25B, pp. 872-873.
Ramesh, D, et al.: Studies on Polycyclic Thiaarenes. Indian J. Chem. Sep. 1986, vol. 25B, pp. 964-965.
Luo et al.; "Tanshinlactone, a Novel Seco-abietanoid from *Salvia miltiorrhiza*" Chem. Pharm. Bull. 34 3166-3168 (1986).
Wang et al.; "Antitumor Agents, 239, Isolation, Structure Elucidation, Total Synthesis, and Anti-Breast Cancer Activity of Neotanshinlactone from *Salvia miltiorrhiza*" J. Med. Chem. 47 5816-5819 (2004).
Wu et al.; "Cytotoxic Activities of Tanshinones Against Human Carcinoma Cell Lines" *American Journal of Chinese Medicine* XIX, 3-4, 207-216 (1991).
Hua DH et al. An improved procedure of the Pechmann condensation in the synthesis of 8-ethyltrimethoxy-6H-benzo[d]naphtha[1,2-b]-pyran-6-ones structurally related to the aglycon of gilvocarcins. J. Org. Chem. 1992; 57: 399-403.
RN 107516-42-7 (see compound).
Hart DJ and Mannino A. Synthesis of defucogilvocarcin V isosteres via MAD-mediated conjugate addition of carbanions to naphthoquinone ketals. Tetrahedron. Mar. 11, 1996; 52(11): 3841-3856.
Seo E-K et al. New bioactive aromatic compounds from *Vismia guianensis*. Phytochemistry. Sep. 1, 2000; 55: 35-42.
Lee D-S and Lee S-H. Biological activity of dihydrotanshinone I: effect on apoptosis. Journal of Bioscience and Bioengineering. 2000; 89(3): 292-293.
Supplementary European Search Report, EP 05 73 1541, Mar. 30, 2009.

* cited by examiner

*Primary Examiner*—Charanjit S Aulakh
(74) *Attorney, Agent, or Firm*—Myers Bigel Sibley & Sajovec, P.A.

(57) ABSTRACT

Compounds of Formulas I-II are described,

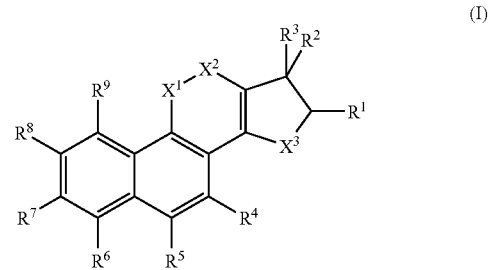

(I)

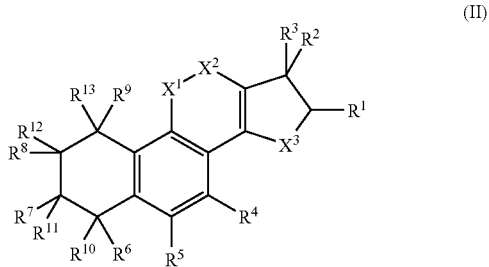

(II)

along with methods of using such compounds for the treatment of cancer and pharmaceutical formulations thereof.

20 Claims, 2 Drawing Sheets

Figure 1. Structures of neo-tanshinlactone (1), tanshinlactone and tanshinones

NEO-TANSHINLACTONE AND ANALOGS AS POTENT AND SELECTIVE ANTI-BREAST CANCER AGENTS

RELATED APPLICATIONS

This application is a continuation of and claims priority to U.S. patent application Ser. No. 11/075,476, filed Mar. 9, 2005, now issued as U.S. Pat. No. 7,495,026, and also claims the benefit of U.S. Provisional Patent Application Ser. No. 60/552,050, filed Mar. 10, 2004, the disclosure of each of which is incorporated by reference herein in its entirety.

STATEMENT OF GOVERNMENT SUPPORT

This invention was made with government support under NIH grant CA 17625. The Government has certain rights to this invention.

FIELD OF THE INVENTION

The present invention concerns active compounds, formulations thereof, and methods of use thereof, particularly in methods of treating cancer.

BACKGROUND OF THE INVENTION

Breast cancer is the most frequent cancer in women and is the second leading cause of cancer-related death and the present breast cancer therapies achieve meaningful clinical results in only 30-40% of patients. (F. Labrie et al., *J. Steroid Biochem. Mol. Biology*, 69 51-84 (1999)). Estrogens are well recognized to play the predominant role in breast cancer development and growth and much effort has been devoted to the blockade of estrogen formation and action (V. C. Jordan and W. J. Gradishar, *Molec. Aspects Med.*, 18, 187-247 (1997)). However, expression of the HER-2 receptor is also a significant factor associated with breast cancer morbidity. (D. J. Slamon, et al, *Science*, 244, 707-712, (1989)). It is also becoming clearer that crosstalk between estrogen and growth factor receptor pathways occurs and likely is a factor in the pathology and treatment of breast cancer. (Y. Kinoshita and S. Chen, *Cancer Res.*, 63, 3546-3555, (2003))

The most widely used therapy for breast cancer, which has shown benefits at all stages of the disease, is the use of an antiestrogen such as tamoxifen. Over thirty years of clinical trials with tamoxifen have not only proven its clinical merits but also highlighted the need for a next generation of drugs that are potentially more efficacious and have fewer side-effects, especially the serious side-effects related to estrogen agonist properties (K. Dhingra, *Investigational New Drugs* 17, 285-311 (1999))

"Tanshen", the rhizome of *Salvia miltiorrhiza* Bunge, has been used in traditional Chinese medicine (TCM) for the treatment of coronary heart diseases, particularly angina pectoris and myocardial infarction. It has also been applied for hemorrhage, dismenorrhea, miscarriage, swelling, and insomnia (S. Y. Ryu et al., *Planta Medica*, 63, 339-342 (1997)). Neo-tanshinlactone (1) was originally isolated from this TCM. Its structure is unique compared to those of other constituents isolated from *S. miltiorrhiza*.

SUMMARY OF THE INVENTION

Neo-tanshinlactone (1) was totally synthesized for the first time and evaluated against several human cancer cell lines. Compound 1 showed selective inhibitory activity against the human breast cancer MCF-7 cell line. Extended bioassay studies showed that compound 1 is active against ER+ human breast cancer (MCF-7 and ZR-75-1) with $ED_{50}$=0.6 µg/mL and 0.3 µg/mL, respectively, but inactive against ER− MDA− cell lines (MB-231 and HS 587-T) with $ED_{50}$>10 µg/mL. Compound 1 is 10-fold more potent and 20-fold more selective against ER+breast cancer in vitro as compared to tamoxifen citrate. Interestingly, 1 was also active against a HER-2-overexpressing breast cancer cell line (SK-BR-3, HER-2++), but was essentially inactive against epidermal growth factor receptor (EGFR) overexpressing skin cancer or androgen receptor (AR)-dependent prostate cancer cell lines (A431 and LN-CaP, respectively). Compound 1 is worthy of further development as an anticancer drug candidate.

Thus, a first aspect of the present invention is the compound neo-tanshinlactone or a pharmaceutically acceptable salt thereof.

A second aspect of the present invention is analogs of neo-tanshinlactone as described herein, and pharmaceutically acceptable salts thereof.

A further aspect of the present invention is a pharmaceutical formulation comprising a compound as described above, and further described below, in a pharmaceutically acceptable carrier (e.g., an aqueous carrier).

A still further aspect of the present invention is a method of treating a cancer, comprising administering to a human or animal subject in need thereof a treatment effective amount (e.g., an amount effective to treat, slow the progression of, etc.) of a compound as described above, and further described below. Examples of cancers that may be treated include, but are not limited to, skin cancer, lung cancer including small cell lung cancer and non-small cell lung cancer, testicular cancer, lymphoma, leukemia, Kaposi's sarcoma, esophageal cancer, stomach cancer, colon cancer, breast cancer, endometrial cancer, ovarian cancer, central nervous system cancer, liver cancer and prostate cancer.

DETAILED DESCRIPTION OF THE INVENTION

Figure 1:
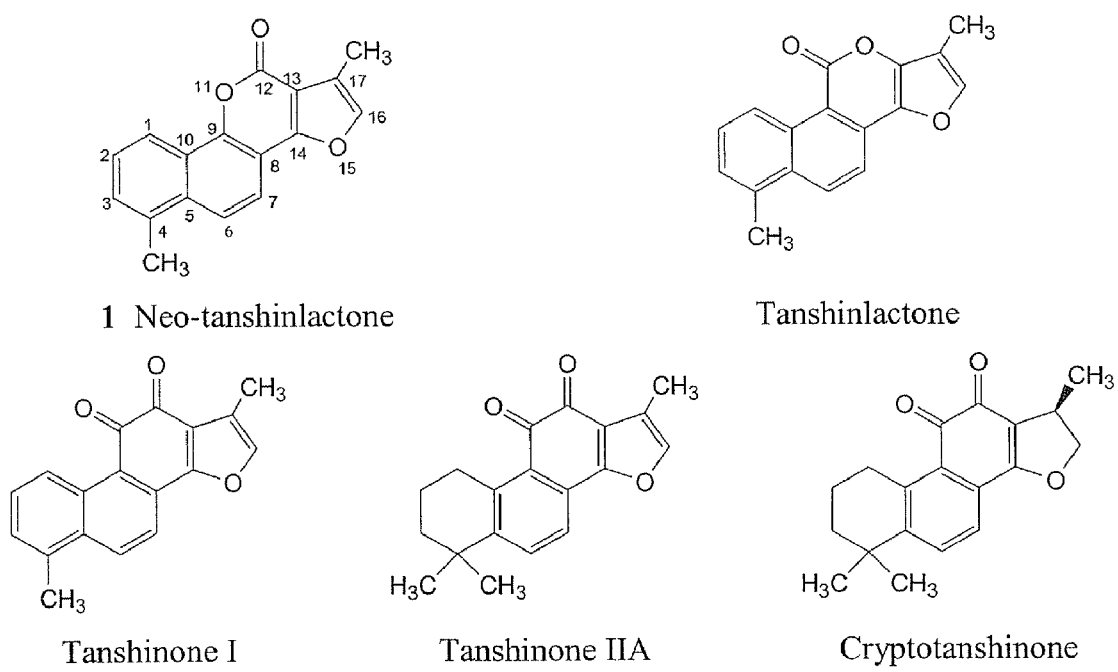
FIG. 1. Structures of neo-tanshinlactone (1), tanshinlactone, and tanshinones.

The present invention will now be described more fully hereinafter. This invention may, however, be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

Unless otherwise defined, all technical and scientific terms used herein have the same meaning as commonly understood by one of ordinary skill in the art to which this invention belongs. All publications, patent applications, patents and other references mentioned herein are incorporated by reference in their entirety.

The term "alkyl" or "loweralkyl" as used herein refers to C1 to C4, C6 or C8 alkyl, which may be linear or branched and saturated or unsaturated.

"Cycloalkyl" is specified as such herein, and is typically C3, C4 or C5 to C6 or C8 cycloalkyl.

"Alkenyl" or "loweralkenyl" as used herein likewise refers to C1 to C4 alkenyl, and alkoxy or loweralkoxy as used herein likewise refers to C1 to C4 alkoxy.

"Alkoxy" as used herein refers to linear or branched, saturated or unsaturated oxo-hydrocarbon chains, including for example methoxy, ethoxy, propoxy, isopropoxy, butoxy, and t-butoxy.

"Alkylogen" as used herein means alkyl or loweralkyl in which one, two, three or more (e.g., all) hydrogens thereon have been replaced with halo. Examples of alkylogen include but are not limited to trifluoromethyl, chloromethyl, 2-chloroethyl, 2-bromoethyl, and 2-iodoethyl. Alkylogens may also be referred to as haloalkyl or perhaloalkyl (e.g. fluoroalkyl; perfluoroalkyl).

The term "aryl" as used herein refers to C3 to C10 cyclic aromatic groups such as phenyl, naphthyl, and the like, and includes substituted aryl groups such as tolyl.

"Halo" as used herein refers to any halogen group, such as chloro, fluoro, bromo, or iodo.

The term "hydroxyalkyl" as used herein refers to C1 to C4 linear or branched hydroxy-substituted alkyl, i.e., —CH$_2$OH, —(CH$_2$)$_2$OH, etc.

The term "aminoalkyl" as used herein refers to C1 to C4 linear or branched amino-substituted alkyl, wherein the term "amino" refers to the group NR'R", wherein R' and R" are independently selected from H or lower alkyl as defined above, i.e., —NH$_2$, —NHCH$_3$, —N(CH$_3$)$_2$, etc.

The term "oxyalkyl" as used herein refers to C1 to C4 oxygen-substituted alkyl, i.e., —OCH$_3$, and the term "oxyaryl" as used herein refers to C3 to C10 oxygen-substituted cyclic aromatic groups.

The term "alkylenedioxy" refers to a group of the general formula —OR'O—, —OR'OR'—, or —R'OR'OR'— where each R' is independently alkyl.

"Treat" or "treating" as used herein refers to any type of treatment that imparts a benefit to a patient afflicted with a disease, including improvement in the condition of the patient (e.g., in one or more symptoms), delay in the progression of the disease, prevention or delay of the onset of the disease, etc.

"Pharmaceutically acceptable" as used herein means that the compound or composition is suitable for administration to a subject to achieve the treatments described herein, without unduly deleterious side effects in light of the severity of the disease and necessity of the treatment.

"Inhibit" as used herein means that a potential effect is partially or completely eliminated.

The present invention is concerned primarily with the treatment of human subjects, but may also be employed for the treatment of other animal subjects (i.e., mammals such as dogs, cats, horses, etc. or avians) for veterinary purposes. Mammals are preferred, with humans being particularly preferred.

A. Active Compounds.

Active compounds of the present invention are described below, and may be formulated and used in the compositions and methods described below.

Active compounds of the invention include compounds of Formula I:

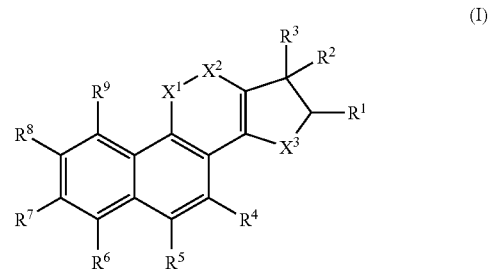

wherein:
$R^1$, $R^2$, $R^3$, $R^4$, $R^5$, $R^6$, $R^7$, $R^8$, and $R^9$ are each independently selected from the group consisting of H, lower alkyl, hydroxy, lower alkoxy, halo, amino, aminoalkyl, nitro, heteroaryl, aryl, OC(=O)$R^{14}$, OC(=O)O$R^{14}$, OC(=O)N($R^{14}$)$_2$, O(CH$_2$)$_m$N($R^{14}$)$_2$, C(=O)N($R^{14}$)$_2$, and O(CH$_2$)$_m$COOH where m is 1-5 and $R^{14}$ is H or lower alkyl;

or $R^1$ and $R^2$ together form a covalent bond;

or $R^2$ and $R^3$ together form =Z, where Z is selected from the group consisting of O, S, and NH;

$X^1$ and $X^2$ are each independently selected from the group consisting of —C($R^{15}$)($R^{16}$)—, O, S, NH, C=O, C=S, C=NH, SO, and SO$_2$, wherein $R^{15}$ and $R^{16}$ are each independently selected from the group consisting of H, lower alkyl, hydroxy, lower alkoxy, halo, amino, aminoalkyl, nitro, heteroaryl, aryl, OC(=O)$R^{17}$, OC(=O)O$R^{17}$, OC(=O)N($R^{17}$)$_2$, O(CH$_2$)$_n$N($R^7$)$_2$, C(=O)N($R^{17}$)$_2$, and O(CH$_2$)$_m$COOH, where m is 1-5 and $R^{17}$ is H or lower alkyl;

or $X^1$ and $X^2$ together form —C=C—;

$X^3$ is selected from the group consisting of O, S, NH, and (CH$_2$)$_p$ where p is 1-3;

or a pharmaceutically acceptable salt thereof.

In some embodiments the compounds of Formula I are subject to the proviso that neo-tanschinlactone is excluded therefrom.

In some embodiments of Formula I, $X^1$ is CH$_2$, S, NH, C=O, C=S, C=NH, SO, or SO$_2$. In other embodiments of Formula I, $X^1$ is O.

In some embodiments of Formula I, $X^2$ is CH$_2$, O, S, NH, C=S, C=NH, SO, or SO$_2$. In other embodiments of Formula I, $X^2$ is C=O.

In some embodiments of Formula I, at least one of, or both of, $X^1$ and $X^2$ are CH$_2$. In some embodiments of Formula I, $X^3$ and $X^2$ together form —C=C—. In some embodiments of Formula I, one of $X^1$ and $X^2$ is CH$_2$ and the other is not.

In some embodiments of Formula I, $X^3$ is $CH_2$, S, or NH.

In some embodiments of Formula I, $X^1$ is not O when $X^2$ is C=O.

In some embodiments of Formula I, $R^1$ and $R^2$ together form a covalent bond.

In some embodiments of Formula I, $R^2$ and $R^3$ together form =Z, where Z is selected from the group consisting of O, S, and NH.

In some embodiments of Formula I, at least one of $R^1$, $R^2$, $R^3$, $R^4$, $R^5$, $R^6$, $R^7$, $R^8$, and $R^9$ is selected from the group consisting of lower alkoxy, halo, amino, aminoalkyl, nitro, heteroaryl, aryl, OC(=O)$R^{14}$, OC(=O)O$R^{14}$, OC(=O)N$(R^{14})_2$, O(CH$_2$)$_m$N$(R^{14})_2$, and C(=O)N$(R^{14})_2$, O(CH$_2$)$_m$COOH where m is 1-5 and $R^{14}$ is H or lower alkyl.

Additional active compounds of the invention are compounds of Formula II:

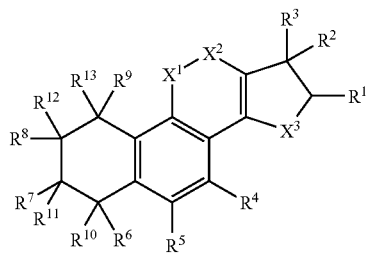

(II)

wherein:

$R^1$, $R^2$, $R^3$, $R^4$, $R^5$, $R^6$, $R^7$, $R^8$, and $R^9$ are each independently selected from the group consisting of H, lower alkyl, hydroxy, lower alkoxy, halo, amino, aminoalkyl, nitro, heteroaryl, aryl, OC(=O)$R^{14}$, OC(=O)O$R^{14}$, OC(=O)N$(R^{14})_2$, O(CH$_2$)$_m$N$(R^{14})_2$, C(=O)N$(R^{14})_2$, and O(CH$_2$)$_m$COOH, where m is 1-5 and $R^{14}$ is H or lower alkyl;

or $R^1$ and $R^2$ together form a covalent bond;

or $R^2$ and $R^3$ together form =Z, where Z is selected from the group consisting of O, S, and NH;

$R^{10}$ and $R^{11}$ are each H or together form a covalent bond;

$R^{12}$ and $R^{13}$ are each H or together form a covalent bond, subject to the proviso that $R^{12}$ and $R^{13}$ do not form a covalent bond if $R^{10}$ and $R^{11}$ form a covalent bond;

$X^1$ and $X^2$ are each independently selected from the group consisting of —C($R^{15}$)($R^{16}$)—, O, S, NH, C=O, C=S, C=NH, SO, and SO$_2$, wherein $R^{15}$ and $R^{16}$ are each independently selected from the group consisting of H, lower alkyl, hydroxy, lower alkoxy, halo, amino, aminoalkyl, nitro, heteroaryl, aryl, OC(=O)$R^{17}$, OC(=O)O$R^7$, OC(=O)N$(R^{17})_2$, O(CH$_2$)$_m$N$(R^{17})_2$, C(=O)N$(R^7)_2$, and O(CH$_2$)$_m$COOH, where m is 1-5 and $R^{17}$ is H or lower alkyl;

or $X^1$ and $X^2$ together form —C=C—;

$X^3$ is selected from the group consisting of O, S, NH, and (CH$_2$)$_p$ where p is 1-3;

or a pharmaceutically acceptable salt thereof.

In some embodiments of Formula II, $X^1$ is $CH_2$, S, NH, C=O, C=S, C=NH, SO, or SO$_2$. In other embodiments of Formula II, $X^1$ is O.

In some embodiments of Formula II, $X^2$ is $CH_2$, O, S, NH, C=S, C=NH, SO, or SO$_2$. In other embodiments of Formula I$^1$, $X^2$ is C=O.

In some embodiments of Formula II, at least one of, or both of, $X^1$ and $X^2$ are $CH_2$. In some embodiments of Formula II, $X^1$ and $X^2$ together form —C=C—. In some embodiments of Formula II, both $X^1$ and $X^2$ are $CH_2$. In some embodiments of Formula II, one of $X^1$ and $X^2$ is $CH_2$ and the other is not.

In some embodiments of Formula II, $X^3$ is $CH_2$, S, or NH.

In some embodiments of Formula II, $X^1$ is not O when $X^2$ is C=O.

In some embodiments of Formula II, $R^1$ and $R^2$ together form a covalent bond.

In some embodiments of Formula II, $R^2$ and $R^3$ together form =Z, where Z is selected from the group consisting of O, S, and NH.

In some embodiments of Formula II, at least one of $R^1$, $R^2$, $R^3$, $R^4$, $R^5$, $R^6$, $R^7$, $R^8$, and $R^9$ is selected from the group consisting of lower alkoxy, halo, amino, aminoalkyl, nitro, heteroaryl, aryl, OC(=O)$R^{14}$, OC(=O)O$R^{14}$, OC(=O)N$(R^{14})_2$, O(CH$_2$)$_m$N$(R^{14})_2$, C(=O)N$(R^{14})_2$, and O(CH$_2$)$_m$COOH, where m is 1-5 and $R^{14}$ is H or lower alkyl.

Active compounds of the invention may be made in the manner described in the Examples and specification below (see, e.g., Schemes 1-2 and accompanying text), and modifications thereof that will be apparent to those skilled in the art. For example, Scheme 3 shows synthetic routes to various active compounds. A solution of aromatic bromide (1 mol) and EtSNa (3 mol) in DMF is heated at reflux for 22 h. After acidification under aq. HCl and extraction with diethyl ether, the thiols are obtained (See, e.g. L. Testaferri et al., *Synthesis* (9), 751-5 (1983); L. Testaferri et al., *Tetrahedron Lett.* 21, 3099-3100 (1990)).

Scheme 3 Synthesis of thio analogs of neo-tanshinlactone

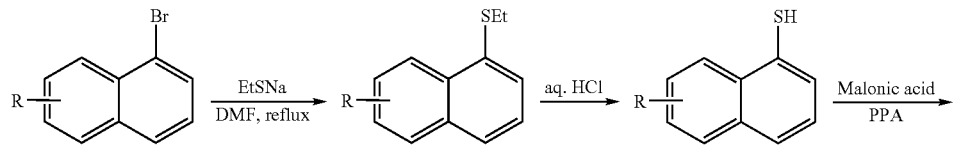

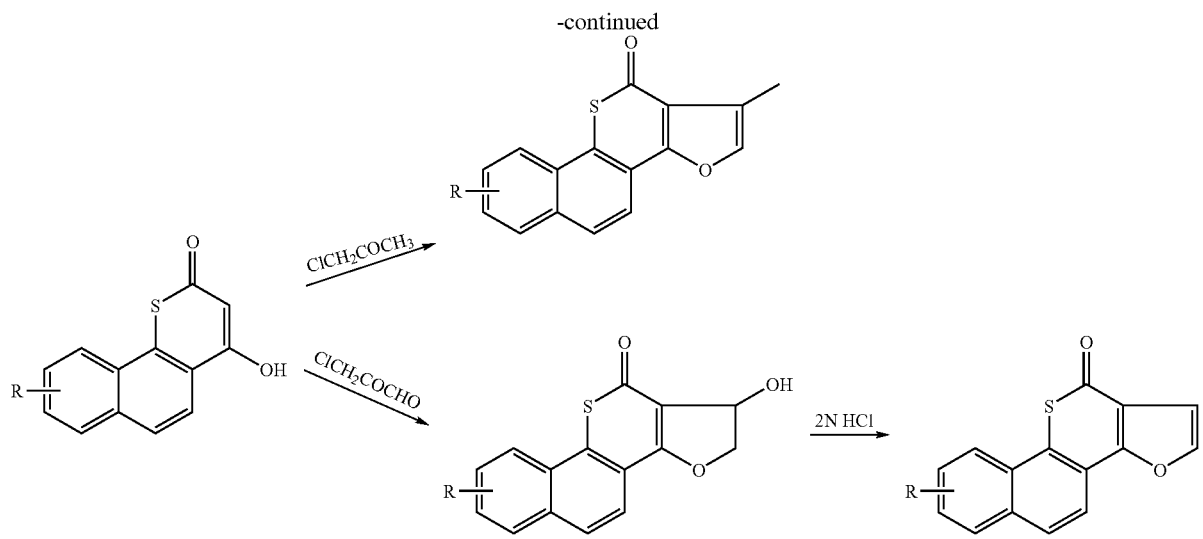

In another example, in Scheme 4 below, additional active compounds are provided by displacing the carbonyl oxygen atom with a sulfur atom using Lawesson's reagent (See, e.g., R. Varma et al., Organic Letters 1(5), 697-700 (1999)).

Scheme 4. Synthesis of thiolactone derivatives

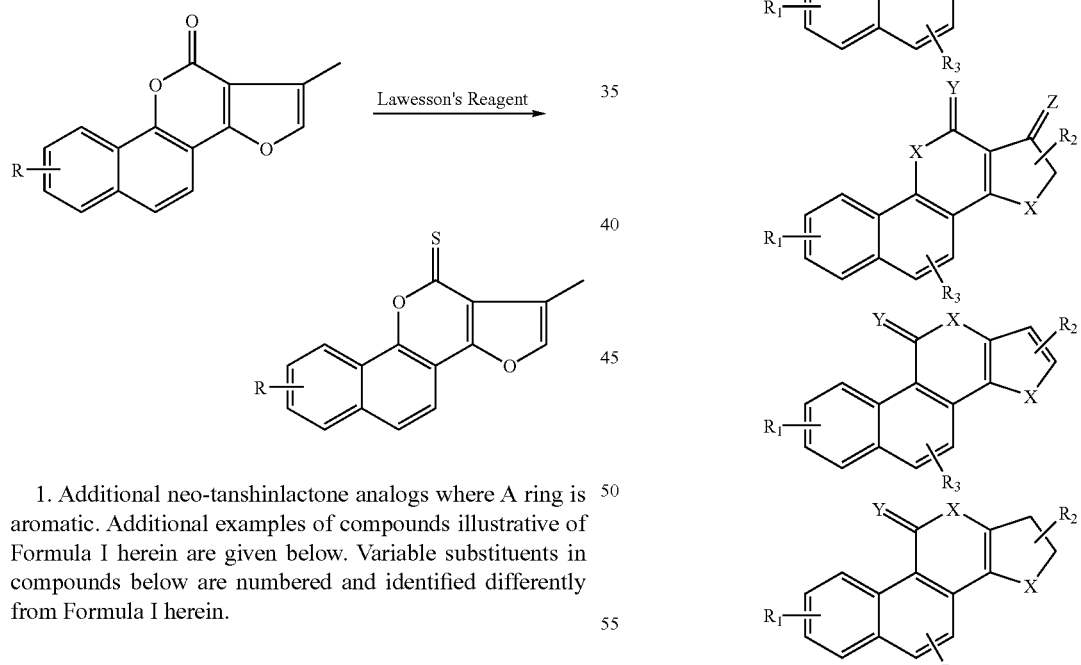

1. Additional neo-tanshinlactone analogs where A ring is aromatic. Additional examples of compounds illustrative of Formula I herein are given below. Variable substituents in compounds below are numbered and identified differently from Formula I herein.

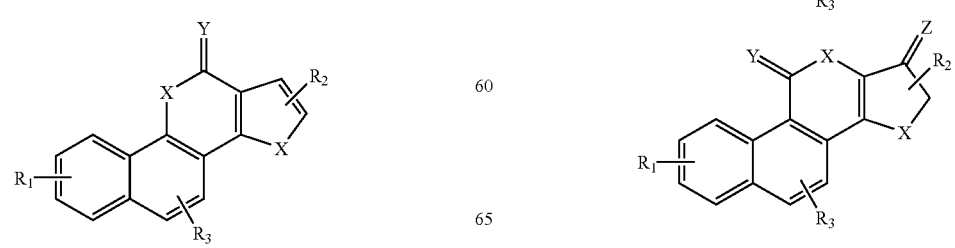

wherein:
X is selected from the group consisting of O, S, or NH;
Y is selected from the group consisting of O, S, or NH
Z is selected from the group consisting of O, S, or NH;
$R^1$-$R_3$ are each independently selected from the group consisting of H, hydroxy, lower alkyl, lower alkoxy, halo, amino, aminoalkyl, nitro, heteroaryl, aryl, OC(=O)$R_4$, OC(=O)O$R_4$, OC(=O)N($R_4$)$_2$, O(CH$_2$)$_m$N($R_4$)$_2$, C(=O)N($R_4$)$_2$, O(CH$_2$)$_m$COOH (m=1-5), in which $R^4$ is H or lower alkyl; or a pharmaceutically acceptable salt thereof.

2. Additional neo-tanshinlactone analogs where A ring is saturated. Examples of compounds of Formula II herein are given below. Variable substituents in compounds below are numbered and identified differently from Formula II herein.

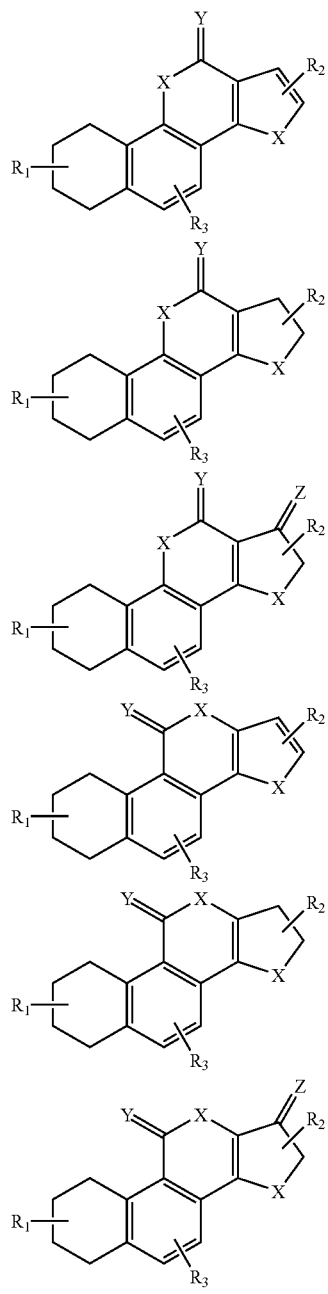

wherein:
X is selected from the group consisting of O, S, or NH;
Y is selected from the group consisting of O, S, or NH
Z is selected from the group consisting of O, S, or NH,
$R_1$-$R_3$ are each independently selected from the group consisting of H, hydroxy, lower alkyl, lower alkoxy, halo, amino, aminoalkyl, nitro, heteroaryl, aryl, OC(=O)$R_4$, OC(=O)O$R_4$, OC(=O)N($R_4$)$_2$, O(CH$_2$)$_m$N($R_4$)$_2$, C(=O)N($R_4$)$_2$, O(CH$_2$)$_m$COOH (m=1-5), in which $R_4$ is H or lower alkyl; or a pharmaceutically acceptable salt thereof.

3. Additional Neo-tanshinlactone analogs where A ring is partially saturated. Additional examples of compounds of Formula II above are given below. Variable substituents in compounds below are numbered and identified differently from Formula II herein.

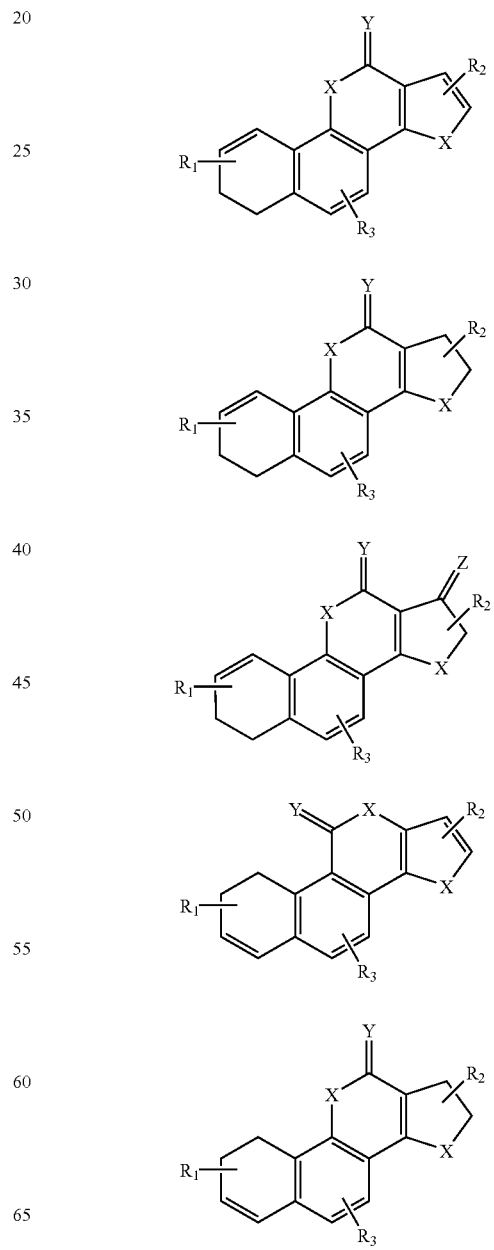

-continued

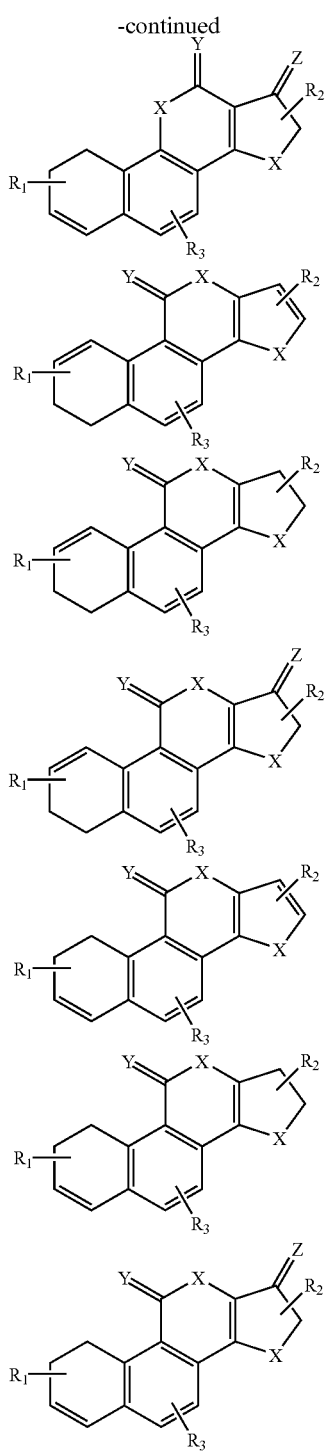

wherein:

X is selected from the group consisting of O, S, or NH;

Y is selected from the group consisting of O, S, or NH

Z is selected from the group consisting of O, S, or NH;

$R_1$-$R_3$ are each independently selected from the group consisting of H, hydroxy, lower alkyl, lower alkoxy, halo, amino, aminoalkyl, nitro, heteroaryl, aryl, OC(=O)$R_4$, OC(=O)OR$_4$, OC(=O)N($R_4$)$_2$, O(CH$_2$)$_m$N($R_4$)$_2$, C(=O)N($R_4$)$_2$, O(CH$_2$)$_n$COOH (m=1-5), in which $R_4$ is H or lower alkyl; or a pharmaceutically acceptable salt thereof.

B. Formulations and Pharmaceutically Acceptable Salts.

The term "active agent" as used herein, includes the pharmaceutically acceptable salts of the compound. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (b) salts formed from elemental anions such as chlorine, bromine, and iodine.

Active agents used to prepare compositions for the present invention may alternatively be in the form of a pharmaceutically acceptable free base of active agent. Because the free base of the compound is less soluble than the salt, free base compositions are employed to provide more sustained release of active agent to the target area. Active agent present in the target area which has not gone into solution is not available to induce a physiological response, but serves as a depot of bioavailable drug which gradually goes into solution.

The compounds of the present invention are useful as pharmaceutically active agents and may be utilized in bulk form. More preferably, however, these compounds are formulated into pharmaceutical formulations for administration. Any of a number of suitable pharmaceutical formulations may be utilized as a vehicle for the administration of the compounds of the present invention.

The compounds of the present invention may be formulated for administration for the treatment of a variety of conditions. In the manufacture of a pharmaceutical formulation according to the invention, the compounds of the present invention and the physiologically acceptable salts thereof, or the acid derivatives of either (hereinafter referred to as the "active compound") are typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.5% to 95% by weight of the active compound. One or more of each of the active compounds may be incorporated in the formulations of the invention, which may be prepared by any of the well-known techniques of pharmacy consisting essentially of admixing the components, optionally including one or more accessory ingredients.

The formulations of the invention include those suitable for oral, rectal, topical, buccal (e.g., sub-lingual), parenteral (e.g., subcutaneous, intramuscular, intradermal, or intravenous) and transdermal administration, although the most suitable route in any given case will depend on the nature and severity of the condition being treated and on the nature of the particular active compound which is being used.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above).

In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising the active compound in a flavoured base, usually sucrose and acacia or tragacanth; and pastilles comprising the compound in an inert base such as gelatin and glycerin or sucrose and acacia.

Formulations of the present invention suitable for parenteral administration conveniently comprise sterile aqueous preparations of the active compound, which preparations are preferably isotonic with the blood of the intended recipient. These preparations may be administered by means of subcutaneous, intravenous, intramuscular, or intradermal injection. Such preparations may conveniently be prepared by admixing the compound with water or a glycine buffer and rendering the resulting solution sterile and isotonic with the blood.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include vaseline, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3:318 (1986)) and typically take the form of an optionally buffered aqueous solution of the active compound. Suitable formulations comprise citrate or bis\tris buffer (pH 6) or ethanol/water and contain from 0.01 to 0.2M active ingredient.

C. Methods of Use.

In addition to the compounds of the formulas described herein, the present invention also provides useful therapeutic methods. For example, the present invention provides a method of inducing cytotoxicity against tumor cells, or treating a cancer or tumor in a subject in need thereof.

Cancer cells which may be inhibited include cells from skin cancer, small cell lung cancer, non-small cell lung cancer, testicular cancer, lymphoma, leukemia, Kaposi's sarcoma, esophageal cancer, stomach cancer, colon cancer, breast cancer, endometrial cancer, ovarian cancer, central nervous system cancer, liver cancer and prostate cancer.

Subjects which may be treated using the methods of the present invention are typically human subjects although the methods of the present invention may be useful for veterinary purposes with other subjects, particularly mammalian subjects including, but not limited to, horses, cows, dogs, rabbits, fowl, sheep, and the like. As noted above, the present invention provides pharmaceutical formulations comprising the compounds of formulae described herein, or pharmaceutically acceptable salts thereof, in pharmaceutically acceptable carriers for any suitable route of administration, including but not limited to oral, rectal, topical, buccal, parenteral, intramuscular, intradermal, intravenous, and transdermal administration.

The therapeutically effective dosage of any specific compound will vary somewhat from compound to compound, patient to patient, and will depend upon the condition of the patient and the route of delivery. As a general proposition, a dosage from about 0.1 to about 50 mg/kg will have therapeutic efficacy, with still higher dosages potentially being employed for oral and/or aerosol administration. Toxicity concerns at the higher level may restrict intravenous dosages to a lower level such as up to about 10 mg/kg, all weights being calculated based upon the weight of the active base, including the cases where a salt is employed. Typically a dosage from about 0.5 mg/kg to about 5 mg/kg will be employed for intravenous or intramuscular administration. A dosage from about 10 mg/kg to about 50 mg/kg may be employed for oral administration.

The present invention is explained in greater detail in the following non-limiting examples.

EXAMPLE 1

Total Synthesis of Compound 1

We report herein for the first time, the total synthesis of compound 1 and its biological activity against several human cancer cell lines.

Neo-tanshinlactone (1) was synthesized by a 8-step sequence, as illustrated in Scheme 1. Our synthetic strategy was to first prepare 8-methyl-1-naphthol (6). Accordingly, 5-methoxy-1-tetralone (2) was reacted with methylmagnesium bromide, and without purification, the resulting crude product (3) was dehydrated using concentrated HCl (Y.-G. Suh et al., *Chem. Commun.*, 1203-1204 (2000); P. Mayer et al., *Heterocycles*, 55(2), 387-392 (2000)). The product 4, after purification, was dehydrogenated over 10% Pd/C in refluxing triglyme to furnish compound 5. Demethylation of 5 with $BBr_3$ gave the desired naphthol intermediate 6 after silica gel chromatography. The total yield over for the four steps (2→6) was 70%. Treatment of 6 with malonic acid in the presence of PPA at 75° C. yielded 7 (H. Kamijo et al., *Nippon Kagaku Kaishi*, 11, 1257-1262 (1993)). Reaction of 7 with chloroacetone under basic conditions in DMF, followed by reaction with PPA at 110° C. gave the target product 1. (Y.-L. Chen et al., *Helvetica Chimica Acta*, 79, 651-657 (1996) B. Rajitha et al., *Indian J. Chem.*, 25B, 872-873 (1986))

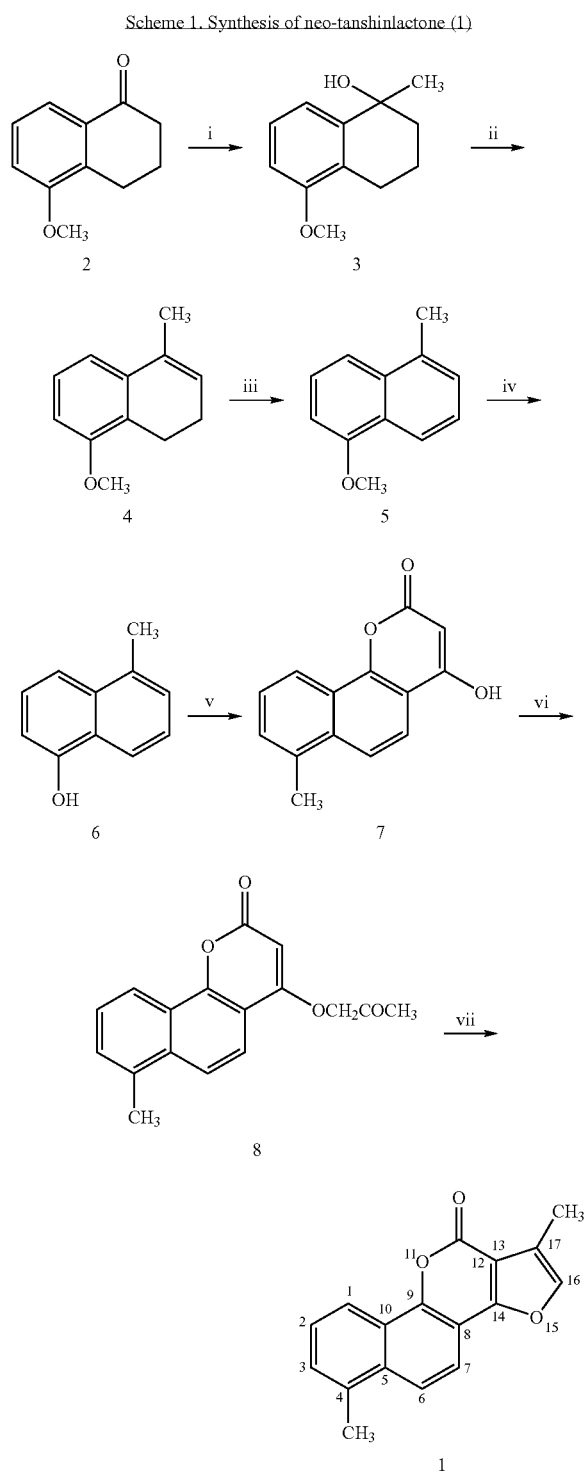

Scheme 1. Synthesis of neo-tanshinlactone (1)

(i) CH₃MgBr, Et₂O, reflux, 5 h; (ii) ZnCl₂/conc. HCl, benezene, 5 h; (iii) 10% Pd/C, triglyme, reflux 3 days; (iv) BBr₃, CH₂Cl₂, reflux, 3 h; (v) malonic acid, PPA, 95-100° C., 4 h; (vi) chloroacetone, K₂CO₃, DMF; (vii) PPA, 110° C., 4 h.

Compound 1 was screened against several human cancer cell lines and showed unique specific activity. It was active against the MCF-7 cancer cell lines at 0.6~1.2 μg/mL but showed insignificant activity against other cell lines in the panel at concentrations up to 10 μg/mL (Table 1).

TABLE 1

Cytotoxicity of Neo-tanshinlactone (1)

| Compound | MCF-7[†] | MDA-MB-231 | A549 |
|---|---|---|---|
| Neo-tashinlactone (1) | <2.5(57) | >20(17) | >20(10) |

[†]Cell line: ED$_{50}$ in μg/mL

Neo-tanshinlactone (1): mp=173-175° C.; ESI-MS: 287 (M+Na)⁺, 265 (M+1)⁺; ¹H NMR (300 MHz, CDCl₃) δ: 8.50 (1H, d, J=8.1 Hz, H-1), 7.94 (1H, d, J=9.0 Hz, H-6), 7.88 (1H, d, J=9.0 Hz, H-7), 7.54 (1H, t, J=7.8 Hz, H-2), 7.46 (1H, d, J=8.1 Hz, H-3), 7.44 (1H, s, H-16), 2.74 (3H, s, 4-CH₃), 2.41 (3H, s, 17-CH₃).

EXAMPLE 2

Improved Synthesis of Compound 1

This synthesis provides compound 1 in fewer steps with better yield than the synthesis set forth in Example 1.

The concentrated ethanolic extract of the root of *S. miltiorrhiza* was suspended in water and then extracted with EtOAc. The EtOAc extract was subjected to repeated silica gel chromatography and preparative TLC to obtain compound 1 (FIG. 1).

Compound 1 was obtained as white needles with a molecular formula of C₁₇H₁₂O₃ determined by HREIMS ([M]+, m/z 264.0786). The IR spectrum showed absorption for a carbonyl group (1726 cm⁻¹). The ¹H and ¹³C NMR spectra of 1 were similar to those of tanshinlactone (FIG. 1), which was isolated from the same species by Luo et al. (*Chem. Pharm. Bull.* 1986, 34, 3166-3168.) The ¹H NMR spectrum (CDCl₃) of 1 revealed an ABX pattern for 1,2,3-aromatic protons at δ 8.42 (d, J=8.0 Hz), 7.49 (t, J=8.0 Hz), and 7.41 (d, J=8.0 Hz), and AB pattern for ortho-aromatic protons at δ 7.84 (d, J=8.5 Hz), and 7.79 (d, J=8.5 Hz), one vinyl proton at δ 7.39 (q, J=1.5 Hz), and two methyls at 2.68 (s) and 2.37 (d, J=1.5 Hz). One signal at δ C 158.7 in the ¹³C NMR spectrum of 1 indicated the presence of a lactone ring. This lactone ring is the major difference between neotanshinlactone and the tanshinones. On the basis of the above information, the carbonyl group could be connected to either C-9 or C-13, and the structure was ambiguous on the basis of previous work (Luo, et al, *Chem. Pharm. Bull.,* 34, 3166-3168, (1986)). We have now determined the location of the carbonyl group by HMBC. The observation of three-bond couplings of the vinyl methyl (H-16) to quaternary carbon C-13 (δC 110.3) and H-1 to quaternary carbon C-9 (δC 149.6) indicated that the carbonyl group should be connected to C-12. Because C-9 is connected to the oxygen atom, C-9 was shifted downfield. The complete assignment of the ¹H and ¹³C NMR signals of 1 was based on extensive COSY, HMQC, and HMBC data. Thus, the compound was established to have structure 1 (FIG. 1) and was named as neo-tanshinlactone.

To confirm neo-tanshinlactone (1)'s unique structure and to obtain this minor phytochemical constituent in larger quantity, we decided that total chemical synthesis was necessary. Our synthetic strategy (Scheme 2) was to first prepare 5-methyl-1-naphthol (6)(Suh, Y.-G. et al., *Chem. Commun* 2000, 1203-1204; Mayer, P. et al., *Heterocycles* 2000, 55, 387-392). Treatment of 6 with malonic acid in the presence of PPA at 75° C. yielded 7 (Kamijo, H. et al., *Nippon Kagaku Kaishi* 1993, 11, 1257-1262). Reaction of 7 with chloroacetone in the presence of HOAc/NH₄OAc in toluene/ethanol (Risitano, F. et al., *Tetrahedron Lett.* 2001, 42, 3503-3505) gave the target product 1. Spectroscopic data of the synthesized product were identical with those of the natural product 1.

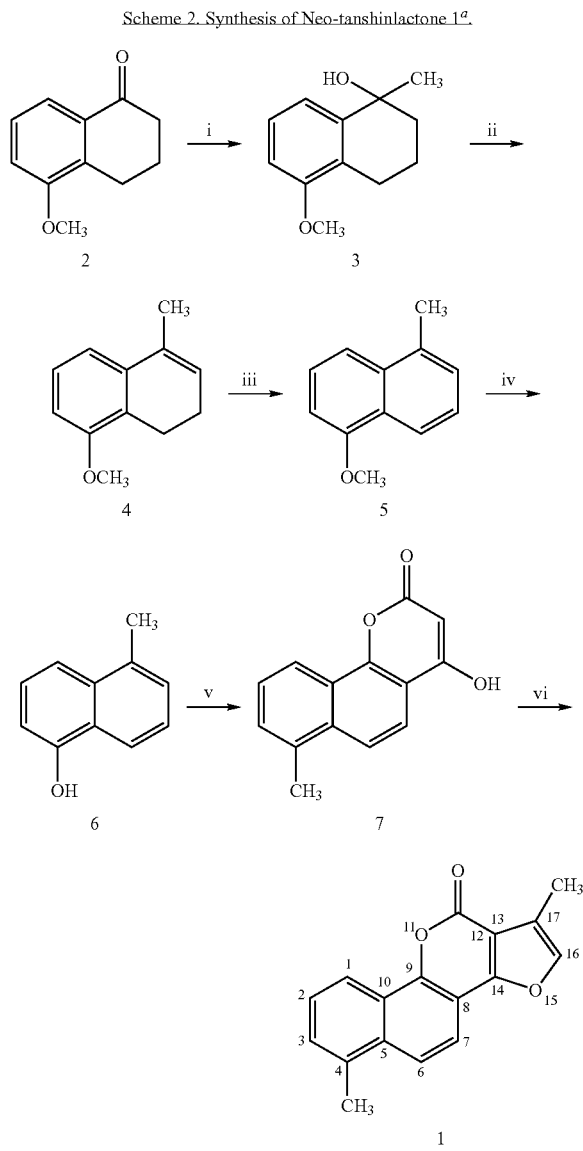

Scheme 2. Synthesis of Neo-tanshinlactone 1[a].

[a](i) CH$_3$MgBr, Et$_2$O, reflux, 5 h; (ii) ZnCl$_2$/concd HCl, benezene, 5 h; (iii) 10% Pd/C, triglyme, reflux 3 days; (iv) BBr$_3$, CH$_2$Cl$_2$, reflux, 3 h; (v) malonic acid, PPA, 75° C., 3 h; (vi) chloroacetone, HOAc/NH$_4$OAc, toluene/EtOH, reflux, 24 h.

Figure 2:
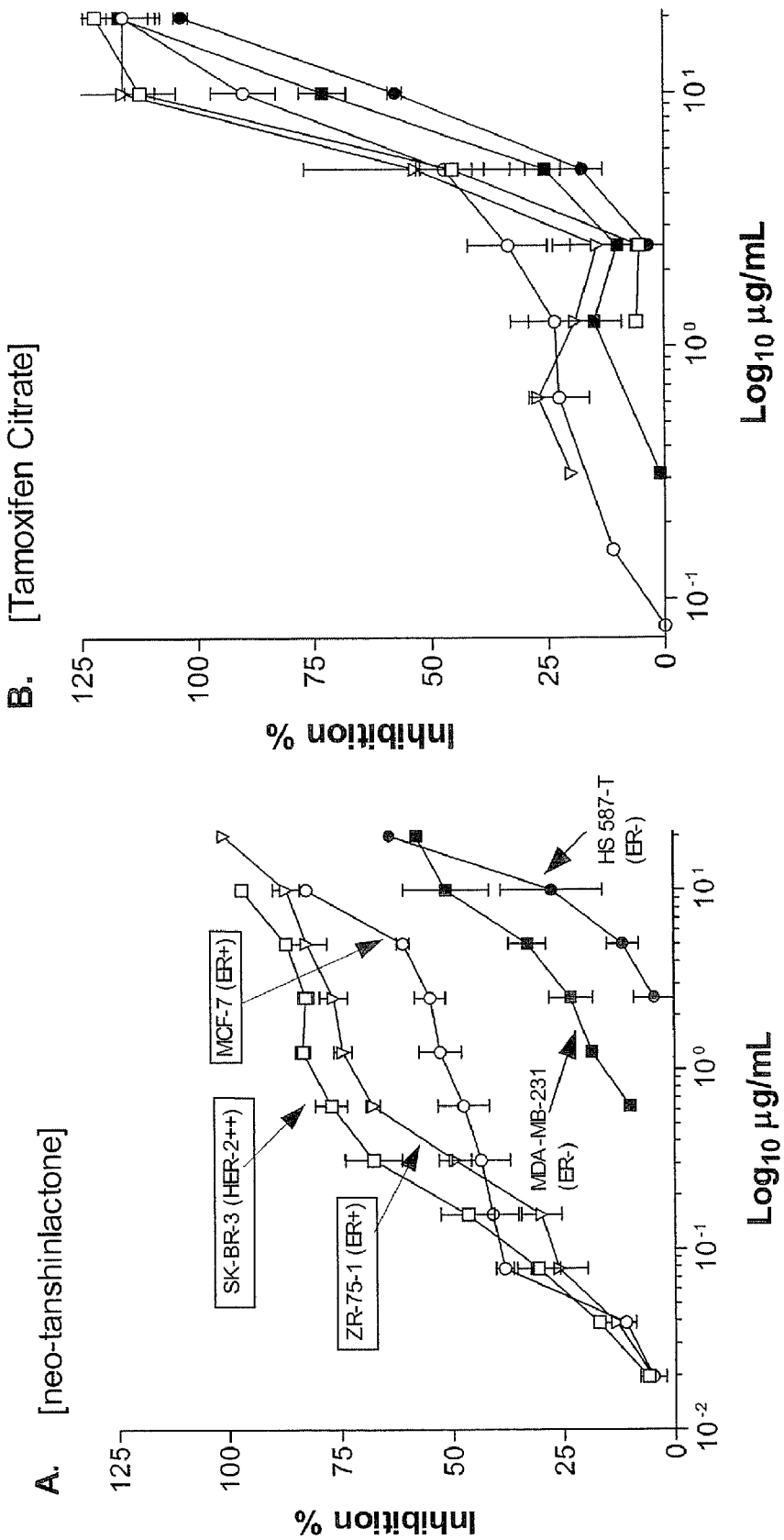
FIG. 2. In vitro anticancer profiles of neo-tanshinlactone and tamoxifen citrate (TAM). Data are mean and standard error from several independent experiments (n=2-4). Neo-tanshinlactone is shown in panel A and tamoxifen citrate is shown in panel B. The specific tumor cells used are: SK-BR-3 (open squares), HS 587-T (closed circles), ZR-75-1 (open triangles), MCF-7 (open circles), MDA-MB-231 (closed squares). Labeled arrows are also used to identify cell lines in panel A to facilitate review.

Extended bioassay studies showed that 1 was active against estrogen receptor positive (ER+) human breast cancer cell lines (MCF-7 and ZR-75-1) with ED$_{50}$ values of 0.6 μg/mL and 0.3 μg/mL, respectively, but was inactive against two ER– cell lines (MDA MB-231, and HS 587-T) with ED50>10 μg/mL (Table 2, FIG. 2).

Interestingly, 1 was also active against a HER-2-overexpressing breast cancer cell line (SK-BR-3, HER-2++), but was essentially inactive against epidermal growth factor receptor (EGFR) overexpressing skin cancer or androgen receptor (AR)-dependent prostate cancer cell lines (A431 and LN-CaP, respectively). The three major tanshinones from *Salvia miltiorrhiza*, tanshinone I, tanshinone IIA, and cryptotanshinone (FIG. 1), were tested against MCF-7 and MDA MB-231 cell lines. The results are shown in Table 3. The selected tanshinones showed significant activity against the two cell lines with ED50 values of <1 ug/mL but without selectivity. We also compared the activity and selectivity of neo-tanshinlactone (1) and tamoxifen citrate (TAM), which is widely used as an estrogen receptor modulator, against four human breast cancer cell lines MCF-7, ZR-75-1, MDA MB-231, and HS 587-T. Tamoxifen citrate was active against ER+ human breast cancers (MCF-7 and ZR-75-1) with ED50 values of 5.0 ug/mL and 3.6 ug/mL, respectively, but was less active against ER– cell lines (MDA MB-231 and HS 587-T) with ED50 values of 7.0 ug/mL and 8.5 ug/mL, respectively (Table 3, FIG. 2). On the basis of these direct comparisons, compound 1 is 10-fold more potent and 20-fold more selective than tamoxifen citrate against ER+ and HER-2++breast cancer in vitro.

In conclusion, we isolated and synthesized a new compound, neo-tanshinlactone (1), with strong and selective anti-breast cancer activity. This compound might be a useful lead for developing novel and promising anti-breast cancer drug candidates. Current data suggest that neo-tanshinlactone (1)'s mechanism of action is complex. It is unlikely to be estrogen-receptor mediated since SK-BR-3 is a receptor-negative cell line (Kinoshita, Y.; Chen, S., *Cancer Res.* 2003, 63, 3546-3555). Effects on estrogen formation were not tested, but MCF-7 has 20-fold lower aromatase activity than SKBR-3, yet the latter cell line is 3-fold more sensitive (Table 2, FIG. 2). Selective target-interaction downstream of the estrogen and HER-2 receptor could account for the activity profile of compound 1 since cross-talk between the signaling pathways is known but not fully understood. Synthesis of analogues of compound 1 is in progress with an aim to further improve the pharmacological profiles for preclinical testing.

TABLE 2

In Vitro Anticancer Profiles of Neo-tanshinlactone (1) and Tamoxifen Citrate (TAM)

| | mean ED$_{50}$ values (μg/mL)/cell line | | | | | | | | | | |
|---|---|---|---|---|---|---|---|---|---|---|---|
| compd | MCF-7 (ER+) | MDA-MB-231 (ER–) | ZR-75-1 (ER+) | HS 587-T (ER–) | SK-BR-3 (ER–) | A431 | LN-CaP | SW620 | PC-3 | KB | KB-VIN |
| 1 | 0.6 | 10 | 0.3 | 16 | 0.2 | >10 (35) | >10 (28-36) | >10 (22) | 10 | >10 (18) | >10 (9) |
| TAM | 5 | 8 | 5 | 9 | 5 | 7 | 6 | 4 | 10 | 9 | 9 |

TABLE 3

Cytotoxicity of Three Major Tanshinones

| compound | MCF-7[a] | MDA-MB-231 |
|---|---|---|
| tanshinone I | 0.82 | 0.75 |
| tanshinone IIA | 0.38 | 0.70 |
| cryptotanshinone | 0.41 | 0.16 |

[a]Cell line: $ED_{50}$ in µg/mL.

Experimental Section

General Experimental Procedures. Melting points were determined with a Yanaco micro-melting point apparatus and are uncorrected. Infrared spectra were obtained on a Nicolet Avatar 320 FTIR spectrophotometer. Nuclear magnetic resonance spectra were recorded on a Varian Unitylnova-500 spectrometer. Chemical shifts are reported in parts per million (δ) units relative to internal tetramethylsilane. The EIMS spectrum was measured on a Finnigan GCQ GC/MS spectrometer at 30 eV. HREIMS was recorded on a Finnigan MAT 95S mass spectrometer. Column chromatography was performed with E. Merck 230-400 mesh silica gel.

Plant Material. The dried roots of *Salvia miltiorrhiza* were purchased from a local herbal drug store in Taipei, and identified by Mr. Jun-Chih Ou, a research fellow of National Research Institute of Chinese Medicine (NRICM). A voucher specimen was deposited in the herbarium of NRICM.

Extraction and Isolation. Slices of the dried roots of *S. miltiorrhiza* (5 kg) were extracted with EtOH (3×10 L) at room temperature. The combined EtOH extracts were concentrated in vacuo. The residue was then partitioned between EtOAc and $H_2O$. The concentrated EtOAc extract (2.2 kg) was subjected to column chromatography over silica gel and eluted with n-hexane/EtOAc (4:1), n-hexane/EtOAc (1:1), and EtOAc successively. The first fraction was rechromatographed on silica gel using a gradient of n-hexane/EtOAc (10:1 to 2:1). The subfraction was further chromatographed on silica gel eluted with n-hexane/$CH_2Cl_2$ (4:1) to give 1 [160 mg, Rf=0.52 (n-hexane/EtOAc=5:1)].

Neo-tanshinlactone (1). White solid (n-hexane/EtOAc); mp 173-175° C.; IR (KBr) îmax 1726, 1619, 1578, 1379, 1172, 1074, 1010, 770 cm$^{-1}$; $^1$H NMR (CDCl$_3$) δ 2.37 (d, J=1.5 Hz, CH$_3$-17), 2.68 (s, CH$_3$-4), 7.39 (d, J=1.5 Hz, H-16), 7.41 (d, J=8.0 Hz, H-3), 7.49 (t, J=8.0 Hz, H-2), 7.79 (d, J=8.5 Hz, H-7), 7.84 (d, J=8.5 Hz, H-6), 8.42 (d, J=8.0 Hz, H-1); $^{13}$C NMR (CDCl$_3$) δ 8.6 (CH$_3$-17), 19.6 (CH$_3$-4), 108.0 (C-8), 110.3 (C-13), 116.6 (C-7), 120.4 (C-17), 120.7 (C-1), 120.8 (C-6), 123.5 (C-10), 126.9 (C-2), 128.9 (C-3), 133.2 (C-5), 134.6 (C-4), 141.1 (C-16), 149.6 (C-9), 158.7 (C-12, C-14); EIMS m/z (%): 264 (100, M+), 184 (13), 165 (9), 128 (9); HREIMS m/z 264.0788 (M$^+$) (Calcd for $C_{17}H_{12}O_3$: 264.0786).

Synthesis of 5-Methyl-1-naphthol (6). 5-Methoxy-1-tetralone (2) (2 g, 11.3 mmol) was dissolved in 50 mL of anhydrous diethyl ether, and methylmagnesium bromide (9.5 mL, 28.4 mmol) was slowly added to the solution at 0° C. The mixture was then heated to reflux and stirred for 3 h. After cooling, the reaction mixture was extracted with diethyl ether. Without purification, the resulting crude product (3) was dehydrated using concentrated HCl and zinc chloride. After purification, the product 4 (1.9 g) was obtained. 10% Pd/C (2.3 g) was added to a solution of 4 in triglyme (15 mL), and the mixture was heated to reflux for 3 days to furnish compound 5 (1.4 g). To a solution of 5 in anhydrous dichloromethane (20 mL) was added a solution of boron tribromide in dichloromethane (1.0 M, 24 mL) dropwise at 0° C. The mixture was heated to reflux and stirred for 3 h to give the desired naphthol intermediate 6 (1.2 g) after silica gel chromatography. The total yield over four steps (2→6) was 70%. mp 93-94° C.; $^1$H NMR (CDCl$_3$) δ 2.67 (s, 3H), 5.30 (s, 1H), 6.83 (d, J=7.5 Hz, 1H), 7.31-7.41 (m, 3H), 7.58 (d, J=8.4 Hz, 1H), 8.06 (d, J=8.1 Hz, 1H).

Synthesis of 4-Hydroxy-7-methyl-benzo[h]chromen-2-one (7). The mixture of 5-methyl-1-naphthol (6) (1.0 g, 6.33 mmol), malonic acid (658 mg, 6.33 mmol), and PPA (10 g) was heated at 75° C. for 3 h. After the reaction, ice-water was added to the black residue. The solid was filtered, dissolved in 10% $Na_2CO_3$ solution, and stirred overnight. The basic solution was filtered, and the filtrate was acidified with 2 N HCl solution until the pH was about 4. The precipitate was then filtered and purified by silica gel chromatography to yield 7 (620 mg, 43%) as a yellow solid. mp 223-225° C.; $^1$H NMR (DMSO-d$_6$) δ 2.69 (s, 3H), 5.70 (s, 1H), 7.57-7.61 (m, 2H), 7.86 (d, J=9.0 Hz, 1H), 7.92 (d, J=9.0 Hz, 1H), 8.23 (d, J=7.5 Hz, 1H), 12.8 (br s, 1H).

Synthesis of Neo-tanshinlactone (1). To a solution of 7 (50 mg, 0.22 mmol) in toluene (8 mL) was added a mixture of HOAc (66 mg, 1.1 mmol) and NH$_4$OAc (80 mg, 1.1 mmol) in EtOH (2 mL) and chloroacetone (103 mg, 1.1 mmol). The mixture was refluxed 24 h. After cooling, the mixture was diluted with $H_2O$ and extracted with EtOAc. The organic layer was dried over $Na_2SO_4$, filtered, and evaporated. The residue was purified by column chromatography to give 1 (35 mg, 60%) as a white solid. The spectroscopic data of synthetic compound 1 were identical with those of the natural product 1.

In Vitro Anticancer Assay (Nakanishi, Y. et al., *J. Med. Chem.* 2003, 46, 3185). All stock cultures were grown in T-25 flasks. Freshly trypsinized cell suspensions were seeded in 96-well microtiter plates at densities of 1500-7500 cells per well with compounds added from DMSO-diluted stock. After 3 days in culture, attached cells were fixed with cold 50% trichloroacetic acid and then stained with 0.4% sulforhodamine B (SRB). The absorbency at 562 nm was measured using a microplate reader after solubilizing the bound dye. The mean ED50 is the concentration of agent that reduces cell growth by 50% under the experimental conditions and is the average from at least three independent determinations that were reproducible and statistically significant (FIG. 2). The following human tumor cell lines were used in the assay: A549 (non small cell lung cancer), MCF-7 (estrogen receptor positive breast cancer), ZR-75-1 (estrogen receptor positive breast cancer), MDA-MB-231 (estrogen receptor negative breast cancer), HS 587-T (estrogen receptor negative breast cancer), SK– BR-3 (HER-2-overexpressing breast cancer), A431 (EGFRoverexpressing skin cancer), LN-CaP (AR-dependent prostate cancer), SW620 (colon cancer), PC-3 (prostate cancer), KB (nasopharyngeal carcinoma), KB-VIN (vincristine-resistant KB subline). All cell lines were obtained from the Lineberger Comprehensive Cancer Center (UNC-CH) or from ATCC (Rockville, Md.) and were cultured in RPMI-1640 medium supplemented with 25 mMHEPES, 0.25% sodium bicarbonate, 10% fetal bovine serum, and 100 µg/mL kanamycin.

EXAMPLE 3

Synthesis and Evaluation of Neo-Tanshinlactone Analogs

In this Example, we describe the synthesis of a series of novel neo-tanshinlactone analogs and their biological activity against several human tumor cell lines.

Chemistry. 5-Methyl-1-naphthol (9b) and 5-ethyl-1-naphthol (9c) were prepared with the same method as in our previously reported method (Wang, X. et al., *J. Med. Chem.* 2004, 47, 5816-5819), as shown in Scheme 5. Compounds 2a, 2c-e, 3a-e, 4a-e were synthesized from various substituted 1-naphthol (9a-e) according to previously described synthetic method of neo-tanshinlactone. Briefly, the substituted 1-naphthol (9a-e) reacted with malonic acid in the presence of polyphosphoric acid (PPA) to provide intermediates 10a-e (Chang, J C et al., *British Journal of Cancer* 2005, 92, 618-624; Wang, X. et al., *J. Med. Chem.* 2004, 47, 5816-5819), as shown in Scheme 6. Compounds 10a, 10c-e reacted with chloroacetone in the presence of HOAc/NH₄OAc to provide target compound 2a, 2c-e (Risitano, F. et al., *Tetrahedron Lett.* 2001, 42, 3503-3505), as shown in Scheme 6. Compounds 10a-e reacted with chloroacetaldehyde in the presence of potassium carbonate to provide compounds 3a-e with a hydroxyl dihydrofuran ring D (Kamijo, H. et al., *Nippon Kagaku Kaishi* 1993, 11, 1257-1262), as shown in Scheme 6. Compounds 3a-e underwent dehydration at 50° C. in the presence of 2N hydrochloride acid to provide compounds 4a-e with a demethyl furan ring D (Kamijo, H. et al., *Nippon Kagaku Kaishi* 1993, 11, 1257-1262), as shown in Scheme 6.

Scheme 5: Synthesis of 5-methyl-1-naphthol (9b) and 5-ethyl-1-naphthol (9c)

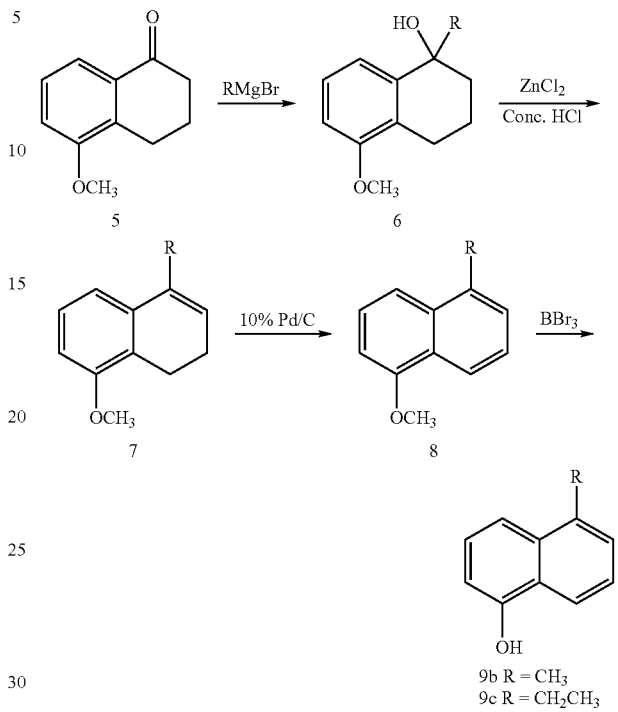

9b R = CH₃
9c R = CH₂CH₃

Scheme 6: Synthetic routes to target compounds

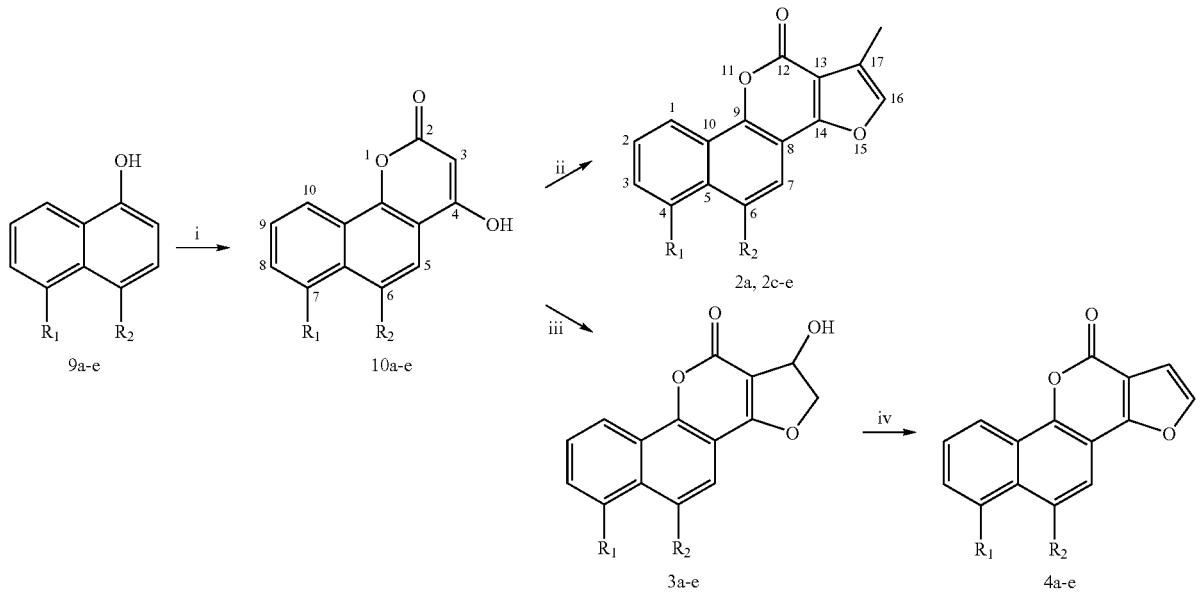

a. R₁ = R₂ = H
b. R₁ = CH₃, R₂ = H
c. R₁ = CH₂CH₃, R₂ = H
d. R₁ = H, R₂ = Cl
e. R₁ = H, R₂ = OCH₃

(i) Malonic acid, PPA, 75° C.; (ii) ClCH₂COCH₃, HOAc/NH₄OAc, toluene/EtOH, reflux, 24 h; (iii) ClCH₂CHO, K₂CO₃, H₂O; (iv) 2 N HCl, 50° C.

Results and Discussion. We synthesized 14 neo-tanshinlactone analogs. All target compounds were tested for cytotoxic activity against several human tumor cell lines. Table 4 shows the results. The Among compounds 2a, 2c-e, compound 2a showed similar activity to tamoxifen with an $ED_{50}$ of 4.0 µg/mL against MCF-7 and ZR-75-1(ER+) and 10.3 and 7.5 µg/mL against MDA MB-231 and HS 587-1 (ER−), respectively. Compound 2c showed better activity than compound 1 with $ED_{50}$ values of 0.45 and 0.18 µg/mL against MCF-7 and ZR-75-1 ($ER^+$) and 10.3 and 7.5 µg/mL against MDA MB-231 and HS 587-1 (ER−), respectively. Compounds 1 and 2c are the most active compounds among all the tested compounds and they showed 10 times better activity and more than 20 times higher selectivity against ER+ cell lines than compound 2a and tamoxifen. We propose that the substituent at the 4-position of neo-tanshinlactone is important for the anticancer activity and compound with ethyl group showed better activity than compound with methyl group, compound with methyl group showed much better activity than compound without substitute at this position. Compounds 2d and 2e with chlorine and methoxy groups, respectively, at the 6-position did not show strong activity. Interestingly, among compounds 3a-e with a hydroxyl dihydrofuran ring, compound 3a showed good activity against MDA-MB-231 (ER−) with an $ED_{50}$ of 3.8 µg/mL, but was ca. fourfold less potent against MCF-7 (ER+) with an $ED_{50}$ of 12.5 µg/mL. Compounds 3b and 3c with methyl and ethyl groups, respectively, at the 4-position showed better activity against the A431 cell line, which over-expresses EGFR, than the remaining cell lines. Thus, for compounds 3a-e, methyl and ethyl groups are beneficial to activity against the A431 cell line, while chlorine and methoxy groups at the 6-position do not affect the activity dramatically. For compounds 4a-e, compound 4b with a 4-methyl group showed better activity than 4a and 4c against the MCF-7 cell line. Compound 4e with a 6-methoxy group showed good activity against the MCF-7, SK-BR-3, and SW620 cell lines with $ED_{50}$ values of 3.4, 4.0, and 4.0 µg/mL, respectively. By comparing the activity of compounds 2a, 3a, and 4a, we can conclude that the methyl group on the furan ring D is critical for the anti-breast cancer activity. The same conclusion can be obtained from other compounds with methyl (1, 3b, vs 4b), ethyl (2c, 3c, vs 4c), chlorine (2d, 3d, vs 4d), and methoxy (2e, 3e, vs 4e) substituents on rings A and B.

Overall, the furan/dihydrofuran ring is critical for the activity and the methyl furan ring resulted in better activity than hydroxyl dihydrofuran and furan rings. In general, methyl and ethyl groups at the 4-position of ring A can increase the activity dramatically, while chlorine and methoxy groups at the 6-position of ring B do not affect the activity significantly. The activity of these compounds does not seem to correlate with ER-status or EGFR/HER2 status.

TABLE 4

Cytotoxicity of compounds against several tumor cell lines

| Compd | MCF-7[†] (ER+) | ZR-75-1 (ER+) | MDA MB-231 (ER−) | HS587-1 (ER−) | SK-BR-3 (ER−, HER2+) | A431 | SW620 | KB |
|---|---|---|---|---|---|---|---|---|
| 2a | 4.0 | 4.0 | 10.3 | 7.5 | | | | |
| 1 | 0.60 | 0.25 | 10.0 | 16.0 | 0.18 | >10 | >10 | >10 |
| 2c | 0.45 | 0.18 | 13.5 | 10 | 0.10 | >10 | >10 | >10 |
| 2d | 5.0 | 8.6 | | | 4.5 | 8.0 | >10 | >10 |
| 2e | 5.0 | >10 | | | 8.6 | 9.5 | 9.0 | >10 |
| 3a | 12.5 | | 3.8 | | | | | |
| 3b | 8.3 | >10 | | | 8.0 | 3.2 | >10 | >10 |
| 3c | 5.0 | | 5.0 | | | 3.0 | | |
| 3d | 5.6 | >10 | | | 8.0 | 7.8 | 4.2 | 9.5 |
| 3e | 5.6 | 5.7 | | | 9.0 | 6.5 | >10 | 6.8 |
| 4a | >20(17) | | 10.5 | | | | | |
| 4b | 5.5 | >10 | | | 8.5 | 8.3 | >10 | >10 |
| 4c | >10 | | >10 | | | | | |
| 4d | 7.0 | >10 | | | >10 | >10 | >10 | >10 |
| 4e | 3.4 | 8.5 | | | 4.0 | 9.5 | 4.0 | 9.5 |
| TAM | 5.0 | 3.6 | 8.5 | 7.0 | 5.0 | 7.0 | 4.0 | 9.0 |

[†]Cell line: $ED_{50}$ in µg/mL. Percent inhibition at the test concentration is the bracketed value.

Materials and Methods. Melting points were measured with a Fisher Johns melting apparatus without correction. The proton nuclear magnetic resonance ($^1$H NMR) spectra were measured on a 300 MHz Varian Gemini 2000 spectrometer using TMS as internal standard. The solvent used was $CDCl_3$ unless indicated. Mass spectra were measured on PE-SCIEX API 3000 with turbo ion spray source or Agilent-1100, LC/MSD-Trap. Thin-layer chromatography (TLC) and preparative TLC were performed on precoated silica gel GF plates purchased from Merck, Inc. Biotage Flash+™ or Isco Companion systems were used for medium pressure column chromatography. Silica gel (200-400 mesh) from Aldrich, Inc. was used for column chromatography. All other chemicals were obtained from Aldrich, Inc.

1-Methoxy-5-ethyl-naphthalene (8). 5-Methoxy-1-tetralone (5) (4 g, 22.6 mmol) was dissolved in 50 mL anhydrous diethyl ether, stirred, and cooled down on ice to 0° C. Ethylmagnesium bromide (19 mL, 56.8 mmol) was added dropwise to the solution, producing copious precipitation. The mixture was then heated to reflux and stirred for 10 h. After cooling, cold water was added slowly to the reaction mixture, which was then extracted with diethyl ether three times. The organic layer was evaporated to afford crude product 6. Without purification, zinc chloride (15 g, 114 mmol) was added to a solution of 6 in benzene (35 mL), then concentrated hydrochloride acid (12 mL) was added to the solution at room temperature. The reaction mixture was heated to reflux for 5 h, cooled, extracted with diethyl ether three times, and the organic layer was evaporated to afford crude product. Purification by column chromatography gave 7 (2 g). To a solution of 7 (2 g) in triglyme (15 mL) was added 10% Pd/C (2 g) and the mixture was heated to reflux for 3 days. After cooling, diethyl ether was added to the mixture and it was filtered on Celite, then washed with diethyl ether to provide compound 8. 50% yield; $^1$H NMR δ 1.37 (3H, t, J=7.8 Hz, $\underline{CH_3}CH_2$—), 3.10 (2H, q, J=7.8 Hz, $CH_3\underline{CH_2}$—), 4.01 (3H, s, $OCH_3$), 6.82 (1H, d, J=7.8 Hz, H-2), 7.36-7.44 (3H, m, H-3, 6, 7), 7.64 (1H, d, J=8.7 Hz, H-4), 815 (1H, d, J=8.4 Hz, H-8).

5-Ethyl-1-naphthol (9c). Anhydrous dichloromethane (20 mL) was added to 8 (870 mg, 4.6 mmol). After cooling to 0° C., $BBr_3$ (boron tribromide 1.0M in dichloromethane) (14 mL, 14 mmol) was added dropwise. The reaction mixture was heated to reflux for 5 h. After cooling, a large amount of water was slowly added and the mixture was extracted three times with dichloromethane. The organic layer was evaporated and the residue was purified on MPLC to afford compound 9c, 75% yield; MS-ESI– (m/z, %): 171 ($M^+$–1, 100), 172 ($M^+$, 45); $^1$H NMR δ 1.37 (3H, t, J=7.8 Hz, $\underline{CH_3}CH_2$—), 3.10 (2H, q, J=7.8 Hz, $CH_3\underline{CH_2}$—), 5.19 (1H, s, OH), 6.82 (1H, d, J=7.8 Hz, H-2), 7.31-7.45 (3H, m, H-3, 6, 7), 7.65 (1H, d, J=8.7 Hz, H-4), 8.06 (1H, d, J=8.1 Hz, H-8).

4-Hydroxy-benzo[h]chromen-2-one (10a). The procedure was identical to that used for the preparation of 10b described above: 30% yield (starting with 1-naphthol 9a); MS-ESI– (m/z,%): 211 ($M^+$–1, 100); $^1$H NMR δ 5.74 (1H, s, H-3), 7.68 (2H, m, H-8, 9), 7.80 (1H, d, J=7.8 Hz, H-5), 7.90 (1H, d, J=7.8 Hz, H-6), 8.00 (1H, m, H-7), 8.50 (1H, m, H-10).

4-Hydroxy-7-ethyl-benzo[h]chromen-2-one (10c). The procedure was identical to that used for the preparation of 10a: 25% yield (starting with 5-ethyl-1-naphthol 9c); $^1$H NMR (DMSO) δ 1.31 (3H, t, J=7.2 Hz, $\underline{CH_3}CH_2$—), 3.12 (2H, q, J=7.2 Hz, $CH_3\underline{CH_2}$—), 5.69 (1H, s, H-3), 7.61 (2H, m, H-8, 9), 7.85 (1H, d, J=8.7 Hz, H-5), 7.99 (1H, d, J=8.7 Hz, H-6), 8.25 (1H, d, J=7.8 Hz, H-10).

4-Hydroxy-6-chloro-benzo[h]chromen-2-one (10d). The procedure was identical to that used for the preparation of 10a: 30% yield (starting with 4-chloro-1-naphthol 9d); $^1$H NMR (DMSO) δ 5.90 (1H, s, H-3), 7.81 (2H, m, H-8, 9), 7.90 (1H, s, H-5), 8.25 (1H, d, J=7.8 Hz, H-7), 8.43 (1H, d, J=7.5 Hz, H-10).

4-Hydroxy-6-methoxy-benzo[h]chromen-2-one (10e). The procedure was identical to that used for the preparation of 10a: 18% yield (starting with 4-methoxy-1-naphthol 9e); $^1$H NMR (DMSO) δ 4.02 (3H, s, $OCH_3$-6), 5.69 (1H, s, H-3), 7.12 (1H, s, H-5), 7.74 (2H, m, H-8, 9), 8.23 (1H, m, H-7), 8.33 (1H, m, H-10).

17-Methyl-11,15-dioxa-cyclopenta[a]phenanthren-12-one (2a). To a solution of 10a (260 mg, 1 mmol) in toluene (25 mL) was added a mixture of HOAc (300 μL, 5 mmol) and ammonium acetate (384 mg, 5 mmol) in EtOH (8 mL) and chloroacetone (420 μL, 5 mmol). The reaction mixture was heated to reflux for 24 h. The mixture was then diluted and extracted with EtOAc. The organic layer was evaporated and the residue was purified on MPLC eluting with hexane:EtOAc=100:1 provided compound 2a, 58% yield; mp 205-207° C.; MS-ESI+(m/z, %): 251 ($M^+$+1, 100), 273 ($M^+$+Na, 65); IR (KBr) 1731, 762 $cm^{-1}$; $^1$H NMR δ 2.41 (3H, d, J=1.2 Hz, $CH_3$-17), 7.45 (1H, d, J=1.2 Hz, H-16), 7.64 (2H, m, H-2, 3), 7.75 (1H, d, J=8.7 Hz, H-7), 7.86 (1H, d, J=8.7 Hz, H-6), 7.90 (1H, m, H-4), 8.62 (1H, dd, J=2.4 Hz, 8.4 Hz, H-1).

4-Ethyl-17-methyl-11,15-dioxa-cyclopenta[a]phenanthren-12-one (2c) The procedure was identical to that used for the preparation of 2a: 49% yield (starting with 10c); mp 145-147° C.; MS-ESI+ (m/z, %): 279 ($M^+$+1, 100); $^1$H NMR δ 1.39 (3H, t, J=7.5 Hz, $\underline{CH_3}CH_2$—), 2.41 (3H, s, $CH_3$-17), 3.15 (2H, q, J=7.5 Hz, $CH_3\underline{CH_2}$—), 7.47 (1H, d, J=1.2 Hz, H-16), 7.48 (1H, d, J=6.9 Hz, H-3), 7.58 (1H, dd, J=6.9 Hz, 8.4 Hz, H-2), 7.87 (1H, d, J=9.0 Hz, H-7), 7.98 (1H, d, J=9.0 Hz, H-6), 8.50 (1H, d, J=8.4 Hz, H-1).

6-Chloro-17-methyl-11,15-dioxa-cyclopenta[a]phenanthren-12-one (2d) The procedure was identical to that used for the preparation of 2a: 55% yield (starting with 10d); mp 220-221° C.; MS-ESI+ (m/z, %): 285 ($M^+$+1, 100), 287 (30); $^1$H NMR δ 2.40 (3H, d, J=1.2 Hz, $CH_3$-17), 7.44 (1H, q, J=1.2 Hz H-16), 7.71 (2H, m, H-2, 3), 7.91 (1H, s, H-7), 8.27 (1H, m, H-4), 8.60 (1H, m, H-1).

6-Methoxy-17-methyl-11,15-dioxa-cyclopenta[a]phenanthren-12-one (2e) The procedure was identical to that used for the preparation of 2a: 45% yield (starting with 48 mg 10e); mp 203-205° C.; LC/MSD-Trap-positive (m/z, %): 303 ($M^+$+Na, 100), 281 ($M^+$+1, 10); $^1$H NMR δ 2.41 (3H, d, J=1.2 Hz, $CH_3$-17), 4.08 (3H, s, $OCH_3$-6), 7.08 (1H, s, H-7), 7.42 (1H, d, J=1.2 Hz, H-16), 7.65 (2H, m, H-2, 3), 8.29 (1H, d, J=8.4 Hz, H-4), 8.55 (1H, d, J=7.5 Hz, H-1).

17-Hydroxy-16,17-dihydro-11,15-dioxa-cyclopenta[a]phenanthren-12-one (3a) To a suspension of 10a (158 mg, 0.75 mmol) in water (5 mL) was added potassium carbonate (155 mg, 1.1 mmol). The resulting mixture was stirred at room temperature for 5 mins, then chloroacetaldehyde (190 μL, 1.5 mmol) was added to the reaction mixture. Stirring was maintained at room temperature for 5 h. Extraction three times with EtOAc and purification on MPLC eluting with $CHCl_3$: MeOH=100:1 provided compound 3a as a white solid, 85% yield; mp 203-205° C.; MS-ESI+ (m/z, %): 277 ($M^+$+Na, 100), 255 ($M^+$+1, 30), 237 ($M^+$+1-$H_2O$, 45); $^1$H NMR δ 4.80 (1H, dd, J=3.0 Hz, 11.1 Hz, H-16α), 4.92 (1H, dd, J=6.9 Hz, 11.1 Hz, H-16β), 5.68 (1H, dd, J=3.0 Hz, 6.9 Hz, H-17), 7.65-7.70 (4H, m, H-2, 3, 6, 7), 7.90 (1H, m, H-4), 8.60 (1H, m, H-1).

17-Hydroxy-4-methyl-16,17-dihydro-11,15-dioxa-cyclopenta[a]phenanthren-12-one (3b) The procedure was identical to that used for the preparation of 3a: 36% yield (starting with 100 mg 10b); amorphous solid; MS-ESI+ (m/z, %): 292 ($M^+$+H+Na, 100); $^1$H NMR δ 2.74 (1H, s, $CH_3$-4), 4.82 (1H, dd, J=2.7 Hz, 11.1 Hz, H-16a), 4.92 (1H, dd, J=7.2 Hz, 11.1 Hz, H-16p), 5.68 (1H, dd, J=2.7 Hz, 7.2 Hz, H-17), 7.55 (2H, m, H-2, 3), 7.70 (1H, d, J=8.7 Hz, H-7), 7.88 (1H, d, J=8.7 Hz, H-6), 8.48 (11H, m, H-1).

4-Ethyl-17-hydroxy-16,17-dihydro-11,15-dioxa-cyclopenta[a]phenanthren-12-one (3c) The procedure was identical to that used for the preparation of 3a: 42% yield (starting with 50 mg 10c); mp 163-165° C.; MS-ESI+ (m/z, %): 283 ($M^+$+1, 40), 265 ($M^+$+1-$H_2O$, 100); $^1$H NMR δ 1.38 (3H, t, J=7.5 Hz, $\underline{CH_3}CH_2$—), 3.13 (2H, q, J=7.5 Hz, $CH_3\underline{CH_2}$—), 4.80 (1H, dd, J=3.0 Hz, 9.9 Hz, H-16c), 4.92 (1H, dd, J=6.9 Hz, 9.9 Hz, H-16p), 5.68 (1H, dd, J=3.0 Hz, 6.9 Hz, H-17), 7.58 (2H, m, H-2, 3), 7.68 (1H, d, J=9.0 Hz, H-7), 7.92 (1H, d, J=9.0 Hz, H-6), 8.40 (1H, d, J=7.8 Hz, H-1).

6-Chloro-17-hydroxy-16,17-dihydro-11,15-dioxa-cyclopenta[a]phenanthren-12-one (3d) The procedure was identical to that used for the preparation of 3a: 15% yield (starting with 260 mg 10d); mp 150° C. (sublime); LC/MSD-Trap-positive (m/z, %): 311 ($M^+$+Na, 100); $^1$H NMR δ 4.82 (1H, dd, J=3.0 Hz, 10.8 Hz, H-16α), 4.92 (1H, dd, J=6.9 Hz, 10.8

Hz, H-16β), 5.66 (1H, dd, J=3.0 Hz, 6.9 Hz, H-17), 7.76 (2H, m, H-2, 3), 7.78 (1H, s, H-7), 8.32 (1H, d, J=8.1 Hz, H-4), 8.62 (1H, d, J=8.4 Hz, H-1).

17-Hydroxy-6-methoxy-16,17-dihydro-11,15-dioxa-cyclopenta[a]phenanthren-12-one (3e) The procedure was identical to that used for the preparation of 3a: 30% yield (starting with 100 mg 10e); mp 210-212° C.; LC/MSD-Trap-positive (m/z, %): 307 (M$^+$+Na, 100); $^1$H NMR δ 4.04 (3H, s, OCH$_3$-6), 4.85 (1H, dd, J=2.7 Hz, 10.8 Hz, H-16α), 4.92 (1H, dd, J=6.9 Hz, 10.8 Hz, H-16β), 5.68 (1H, dd, J=2.7 Hz, 6.9 Hz, H-17), 6.86 (1H, s, H-7), 7.68 (2H, m, H-2, 3), 8.31 (1H, m, H-4), 8.53 (1H, m, H-1).

11,15-Dioxa-cyclopenta[a]phenanthren-12-one (4a) To a suspension of compound 3a (58 mg) in water (4 mL) was added 2N hydrochloride acid and stirring continued at 50° C. until the reaction was complete as monitored by TLC. After extracting with CHCl$_3$ three times, the organic layer was evaporated and the residue was purified on MPLC to provide compound 4a as a solid, 52% yield; mp 198-200° C.; MS-ESI+ (m/z, %): 237 (M$^+$+1, 100); $^1$H NMR (Acetone-d$_6$) δ 7.12 (1H, d, J=2.4 Hz, H-17), 7.73 (2H, m, H-2, 3), 7.93 (1H, d, J=8.7 Hz, H-7), 7.97 (1H, d, J=8.7 Hz, H-6), 8.06 (2H, m, H-4, 16), 8.50 (1H, m, H-1).

4-Methyl-11,15-dioxa-cyclopenta[a]phenanthren-12-one (4b) The procedure was identical to that used for the preparation of 4a: 86% yield (starting with 12 mg 3b); mp 220-222° C.; LC/MSD-Trap-positive (m/z, %): 273 (M$^+$+Na, 100), 251 (M$^+$+1, 45); $^1$H NMR δ 2.75 (1H, s, CH$_3$-4), 7.07 (1H, d, J=2.7 Hz, H-17), 7.53 (2H, m, H-2, 3), 7.69 (1H, d, J=2.7 Hz, H-16), 7.92 (1H, d, J=8.7 Hz, H-7), 7.96 (1H, d, J=8.7 Hz, H-6), 8.50 (1H, d, J=8.1 Hz, H-1).

4-Ethyl-11,15-dioxa-cyclopenta[a]phenanthren-12-one (4c) The procedure was identical to that used for the preparation of 4a: 74% yield (starting with 10 mg 3c); mp 173-174° C.; MS-ESI+ (m/z, %): 265 (M$^+$+1, 100); $^1$H NMR δ 1.40 (3H, t, J=7.5 Hz, $\underline{CH_3}$CH$_2$—), 3.15 (2H, q, J=7.5 Hz, CH$_3$$\underline{CH_2}$—), 7.07 (1H, d, J=2.4 Hz, H-17), 7.50 (1H, d, J=6.3 Hz, H-3), 7.59 (1H, dd, J=6.3 Hz, 8.4 Hz, H-2), 7.69 (1H, d, J=2.4 Hz, H-16), 7.92 (1H, d, J=9.0 Hz, H-7), 8.02 (1H, d, J=9.0 Hz, H-6), 8.52 (1H, d, J=8.4 Hz, H-1).

6-Chloro-11,15-dioxa-cyclopenta[a]phenanthren-12-one (4d) The procedure was identical to that used for the preparation of 4a: 88% yield (starting with 20 mg 3d); mp 150° C. (sublime); MS-ESI+ (m/z, %): 271 (M$^+$+1, 100), 273 (30); $^1$H NMR δ 7.07 (1H, d, J=1.8 Hz, H-17), 7.70 (1H, d, J=1.8 Hz, H-16), 7.76 (2H, m, H-2, 3), 8.01 (1H, s, H-7), 8.32 (1H, m, H-4), 8.64 (1H, m, H-1).

6-Methoxy-11,15-dioxa-cyclopenta[a]phenanthren-12-one (4e) The procedure was identical to that used for the preparation of 4a: 85% yield (starting with 12 mg 3e); mp 194-195° C.; LC/MSD-Trap-positive (m/z, %): 267 (M$^+$+1, 100), 289 (M$^+$+Na, 30); $^1$H NMR δ 4.11 (1H, s, OCH$_3$-6), 7.07 (1H, d, J=2.1 Hz, H-17), 7.13 (1H, s, H-7), 7.68 (3H, m, H-2, 3, 16), 8.31 (1H, dd, J=1.8 Hz, 6.9 Hz, H-4), 8.57 (1H, dd, J=1.8 Hz, 7.8 Hz, H-1).

Biological assay. All stock cultures are grown in T-25 flasks. Freshly trypsinized cell suspensions were seeded in 96-well microtitre plates at densities of 1500-7500 cells per well with compounds added from DMSO-diluted stock. After 3 days in culture, attached cells were fixed with cold 50% trichloroacetic acid and then stained with 0.4% sulforhodamine B (SRB). The absorbency at 562 nm was measured using a microplate reader after solubilizing the bound dye. The mean ED$_{50}$ is the concentration of agent that reduces cell growth by 50% under the experimental conditions and is the average from at least three independent determinations that were reproducible and statistically significant. The following human tumor cell lines were used in the assay: A549 (non-small cell lung cancer), MCF-7 (estrogen receptor positive breast cancer), ZR-75-1 (estrogen receptor positive breast cancer), MDA MB-231 (estrogen receptor negative breast cancer), HS 587-T (estrogen receptor negative breast cancer), SK-BR-3 (estrogen receptor negative, HER-2 over-expressing breast cancer), A431 (EGFR over-expressing skin cancer), LN-CaP (AR-dependent prostate cancer), SW620 (colon cancer), PC-3 (prostate cancer), KB (nasopharyngeal carcinoma), KB-V$_{IN}$ (Vincristine resistant KB subline). All cell lines were obtained from the Lineberg Cancer Center (UNC-CH) or from ATCC (Rockville, Md.) and were cultured in RPMI-1640 medium supplemented with 25 mM HEPES, 0.25% sodium bicarbonate, 10% fetal bovine serum, and 100 μg/mL kanamycin.

The foregoing is illustrative of the present invention, and is not to be construed as limiting thereof. The Invention is defined by the following claims, with equivalents of the claims to be included therein.

What is claimed is:

1. A compound of Formula I:

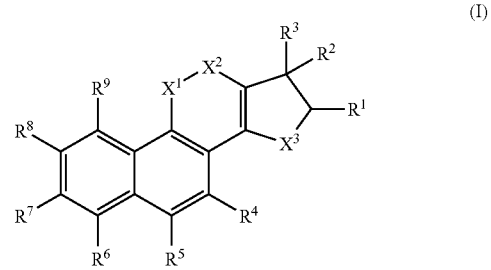

wherein:
R$^3$, R$^4$, R$^5$, R$^6$, R$^8$, and R$^9$ are each independently selected from the group consisting of H, lower alkyl, hydroxy, lower alkoxy, halo, amino, aminoalkyl, and nitro;

R$^7$ is selected from the group consisting of H, lower alkyl, hydroxy, halo, amino, aminoalkyl, and nitro;

R$^1$ and R$^2$ together form a covalent bond;

X$^1$ is selected from the group consisting of O, S, NH, SO, and SO$_2$;

X$^2$ is selected from the group consisting of C=O, C=S, and C=NH;

X$^3$ is selected from the group consisting of O, S, and NH;

or a pharmaceutically acceptable salt thereof;

subject to the proviso that neo-tanshinlactone is excluded therefrom.

2. A compound of Formula II:

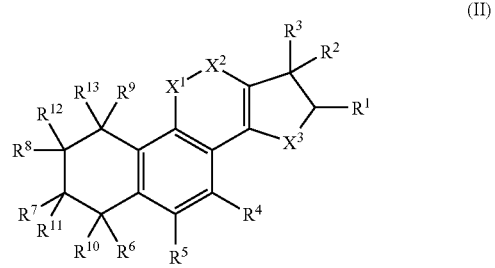

wherein:
R$^3$, R$^4$, R$^5$, R$^6$, R$^7$, R$^8$, and R$^9$ are each independently selected from the group consisting of H, lower alkyl, hydroxy, lower alkoxy, halo, amino, aminoalkyl, and nitro;
R$^1$ and R$^2$ together form a covalent bond;
R$^{10}$ and R$^{11}$ are each H or together form a covalent bond;
R$^{12}$ and R$^{13}$ are each H or together form a covalent bond, subject to the proviso that R$^{12}$ and R$^{13}$ do not form a covalent bond if R$^{10}$ and R$^{11}$ form a covalent bond;
X$^1$ is selected from the group consisting of O, S, NH, SO, and SO$_2$;
X$^2$ is selected from the group consisting of C=O, C=S, and C=NH;
X$^3$ is selected from the group consisting of O, S, and NH; or a pharmaceutically acceptable salt thereof.

3. A pharmaceutical formulation comprising a compound of claim 1 in a pharmaceutically acceptable carrier.

4. The pharmaceutical formulation of claim 3, wherein said carrier is an aqueous carrier.

5. A pharmaceutical formulation comprising a compound of claim 2 in a pharmaceutically acceptable carrier.

6. The pharmaceutical formulation of claim 5, wherein said carrier is an aqueous carrier.

7. A method of treating a cancer, comprising administering to a human or animal subject in need thereof a treatment effective amount of a compound of Formula I:

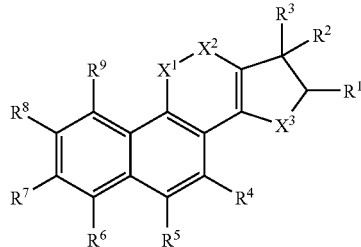

(I)

wherein:
R$^3$, R$^4$, R$^5$, R$^6$, R$^7$, R$^8$, and R$^9$ are each independently selected from the group consisting of H, lower alkyl, hydroxy, lower alkoxy, halo, amino, aminoalkyl, and nitro;
R$^1$ and R$^2$ together form a covalent bond;
X$^1$ is selected from the group consisting of O, S, NH, SO, and SO$_2$;
X$^2$ is selected from the group consisting of C=O, C=S, and C=NH;
X$^3$ is selected from the group consisting of O, S, and NH; or a pharmaceutically acceptable salt thereof; and
wherein said cancer is breast cancer.

8. A method of treating a cancer, comprising administering to a human or animal subject in need thereof a treatment effective amount of a compound of Formula II:

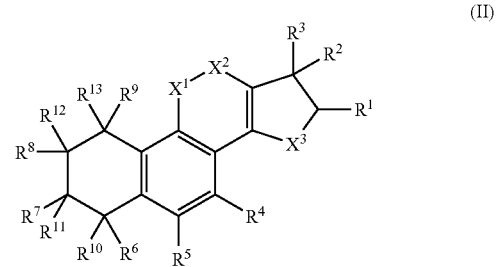

(II)

wherein:
R$^3$, R$^4$, R$^5$, R$^6$, R$^7$, R$^8$, and R$^9$ are each independently selected from the group consisting of H, lower alkyl, hydroxy, lower alkoxy, halo, amino, aminoalkyl, and nitro;
R$^1$ and R$^2$ together form a covalent bond;
R$^{10}$ and R$^{11}$ are each H or together form a covalent bond;
R$^{12}$ and R$^{13}$ are each H or together form a covalent bond, subject to the proviso that R$^{12}$ and R$^{13}$ do not form a covalent bond if R$^{10}$ and R$^{11}$ form a covalent bond;
X$^1$ is selected from the group consisting of O, S, NH, SO, and SO$_2$;
X$^2$ is selected from the group consisting of C=O, C=S, and C=NH,
X$^3$ is selected from the group consisting of O, S, and NH; or a pharmaceutically acceptable salt thereof; and
wherein said cancer is breast cancer.

9. The compound of claim 1, wherein R$^3$, R$^4$, R$^5$, R$^6$, R$^7$, R$^8$, and R$^9$ are each independently selected from the group consisting of H, lower alkyl, hydroxy, and halo.

10. The compound of claim 9, wherein R$^3$, R$^4$, R$^5$, R$^6$, R$^7$, R$^8$, and R$^9$ are each independently selected from the group consisting of H and lower alkyl.

11. The compound of claim 10, wherein R$^3$ is lower alkyl.

12. The compound of claim 2, wherein R$^3$, R$^4$, R$^5$, R$^6$, R$^7$, R$^8$, and R$^9$ are each independently selected from the group consisting of H, lower alkyl, hydroxy, lower alkoxy, and halo.

13. The compound of claim 12, wherein R$^3$, R$^4$, R$^5$, R$^6$, R$^7$, R$^8$, and R$^9$ are each independently selected from the group consisting of H and lower alkyl.

14. The compound of claim 13, wherein R$^3$ is lower alkyl.

15. The method of claim 7, wherein R$^3$, R$^4$, R$^5$, R$^6$, R$^7$, R$^8$, and R$^9$ are each independently selected from the group consisting of H, lower alkyl, hydroxy, lower alkoxy, and halo.

16. The method of claim 15, wherein R$^3$, R$^4$, R$^5$, R$^6$, R$^7$, R$^8$, and R$^9$ are each independently selected from the group consisting of H and lower alkyl.

17. The method of claim 16, wherein R$^3$ is lower alkyl.

18. The method of claim 8, wherein R$^3$, R$^4$, R$^5$, R$^6$, R$^7$, R$^8$, and R$^9$ are each independently selected from the group consisting of H, lower alkyl, hydroxy, lower alkoxy, and halo.

19. The method of claim 18, wherein R$^3$, R$^4$, R$^5$, R$^6$, R$^7$, R$^8$, and R$^9$ are each independently selected from the group consisting of H and lower alkyl.

20. The method of claim 19, wherein R$^3$ is lower alkyl.

* * * * *

UNITED STATES PATENT AND TRADEMARK OFFICE
CERTIFICATE OF CORRECTION

PATENT NO.        : 7,795,299 B2                                                Page 1 of 1
APPLICATION NO.   : 12/355309
DATED             : September 14, 2010
INVENTOR(S)       : Lee et al.

It is certified that error appears in the above-identified patent and that said Letters Patent is hereby corrected as shown below:

In the Specification:

Column 4, Line 47: Please correct "$O(CH_2)_nN(R_7)_2$" to read -- $O(CH_2)_mN(R_7)_2$ --
        Line 65: Please correct "Formula I, $X^3$" to read -- Formula I, $X^1$ --
        Line 66: Please correct "—C≡C—" to read -- —C=C— --

Column 6, Line 4: Please correct "$OC(=O)OR^7$" to read -- $OC(=O)OR^{17}$ --
        Line 5: Please correct "$C(=O)N(R^7)_2$" to read -- $C(=O)N(R^{17})_2$ --

Column 12, Line 1: Please correct "$O(CH_2)_nCOOH$" to read -- $O(CH_2)_mCOOH$ --

Column 19, Line 19: Please correct "(6)" to read -- (δ) --

Column 26, Line 46: Please correct "H-16a)" to read -- H-16α) --
        Line 47: Please correct "H-16p)" to read -- H-16β) --
        Line 57: Please correct "H-16c)" to read -- H-16α) --
        Line 58: Please correct "H-16p)" to read -- H-16β) --

Signed and Sealed this
Twenty-second Day of February, 2011

David J. Kappos
*Director of the United States Patent and Trademark Office*